United States Patent [19]
Yanagida et al.

[11] Patent Number: 6,024,941
[45] Date of Patent: Feb. 15, 2000

[54] EXTERNAL SKIN TREATMENT COMPOSITION

[75] Inventors: Takeshi Yanagida; Okihiko Sakamoto, both of Yokohama, Japan

[73] Assignee: Shiseido Company, Ltd., Tokyo, Japan

[21] Appl. No.: 08/429,905

[22] Filed: Apr. 27, 1995

Related U.S. Application Data

[62] Division of application No. 08/204,286, Mar. 10, 1994, Pat. No. 5,484,816.

[30] Foreign Application Priority Data

| Jul. 13, 1992 | [JP] | Japan | 4-227725 |
| Jul. 13, 1992 | [JP] | Japan | 4-227727 |
| Jul. 13, 1992 | [JP] | Japan | 4-227728 |
| Jul. 13, 1992 | [JP] | Japan | 4-227729 |
| Jul. 13, 1992 | [JP] | Japan | 4-227730 |
| Jul. 13, 1992 | [JP] | Japan | 4-227731 |
| Jul. 13, 1992 | [JP] | Japan | 4-227732 |
| Jul. 13, 1992 | [JP] | Japan | 4-227733 |
| Jul. 13, 1992 | [JP] | Japan | 4-227734 |
| Jul. 13, 1992 | [JP] | Japan | 4-227735 |
| Jul. 13, 1992 | [JP] | Japan | 4-227736 |
| Jul. 13, 1992 | [JP] | Japan | 4-227737 |
| Jul. 13, 1992 | [JP] | Japan | 4-227738 |
| Jul. 13, 1992 | [JP] | Japan | 4-227739 |

[51] Int. Cl.[7] .................................. A61K 7/42
[52] U.S. Cl. ..................... 424/59; 424/70.1; 424/401; 514/725; 514/844; 514/845; 514/846; 514/847; 514/848; 514/861; 514/863; 514/864; 514/880
[58] Field of Search .................. 424/59, 70.1, 401; 514/725, 844, 845, 946, 847, 848, 861, 863, 864, 880

[56] References Cited

U.S. PATENT DOCUMENTS

| Re. 33,845 | 3/1992 | Schreuder | 424/59 |
| 4,011,323 | 3/1977 | Thompson | 424/59 |
| 4,154,823 | 5/1979 | Schutt | 424/60 |
| 4,247,547 | 1/1981 | Marks . | |
| 4,248,861 | 2/1981 | Schutt | 424/60 |
| 4,333,924 | 6/1982 | Bowley et al. | 424/59 |
| 4,371,673 | 2/1983 | Pitha . | |
| 4,454,159 | 6/1984 | Musher | 424/59 |
| 4,464,394 | 8/1984 | Bollag | 424/59 |
| 4,481,186 | 11/1984 | Deckner | 424/59 |
| 4,505,902 | 3/1985 | Millard | 424/195.1 |
| 4,603,046 | 7/1986 | Georgalas et al. | 424/59 |
| 4,604,281 | 8/1986 | Deckner et al. | 424/59 |
| 4,695,452 | 9/1987 | Gannis et al. | 424/59 |
| 4,740,432 | 4/1988 | Bosserelle | 424/59 |
| 4,742,066 | 5/1988 | Deckner et al. | 514/311 |
| 4,764,505 | 8/1988 | Fujinuma et al. | 514/25 |
| 4,769,234 | 9/1988 | Pines et al. | 424/59 |
| 4,783,332 | 11/1988 | Schreuder | 434/59 |
| 4,847,267 | 7/1989 | Deckner et al. | 514/456 |
| 4,863,970 | 9/1989 | Patel et al. | 514/947 |
| 4,882,359 | 11/1989 | Makagawa et al. | 514/947 |
| 4,906,457 | 3/1990 | Ryan | 424/59 |
| 4,938,960 | 7/1990 | Ismail | 514/887 |
| 4,948,577 | 8/1990 | Hara | 424/59 |
| 4,970,216 | 11/1990 | Deckner et al. | 514/311 |
| 4,978,523 | 12/1990 | Motegi et al. | 424/59 |
| 4,985,455 | 1/1991 | Motono | 424/59 |
| 5,000,937 | 3/1991 | Grollier et al. | 424/47 |
| 5,037,850 | 8/1991 | Elliott et al. | 514/529 |
| 5,061,480 | 10/1991 | Marchese et al. | 424/59 |
| 5,082,661 | 1/1992 | Melnik et al. | 424/408 |
| 5,093,511 | 3/1992 | Yoshida et al. | 556/440 |
| 5,135,913 | 8/1992 | Pickart | 514/16 |
| 5,137,725 | 8/1992 | Handjani et al. | 424/450 |
| 5,173,301 | 12/1992 | Itoh et al. | 424/448 |
| 5,213,799 | 5/1993 | Goring et al. | 424/401 |
| 5,244,665 | 9/1993 | Natraj | 424/59 |
| 5,246,611 | 9/1993 | Trinh | 252/8.6 |
| 5,268,180 | 12/1993 | Morancais et al. | 424/450 |
| 5,281,196 | 1/1994 | Sultenfuss | 604/20 |
| 5,298,528 | 3/1994 | Evers | 514/650 |
| 5,310,730 | 5/1994 | Fujinuma et al. | 514/25 |
| 5,348,943 | 9/1994 | Pickart | 514/18 |

FOREIGN PATENT DOCUMENTS

| 0 440 398 | 8/1991 | European Pat. Off. . |
| 2 247 203 | 5/1975 | France . |
| 58-041 813 | 11/1983 | Japan . |
| 62-419 | 1/1987 | Japan . |
| 63-2926 | 1/1988 | Japan . |
| 63-135309 | 6/1988 | Japan . |
| 1-186811 | 7/1989 | Japan . |
| 1-246208 | 10/1989 | Japan . |
| 2-142713 | 5/1990 | Japan . |
| 86/06275 | 11/1986 | WIPO . |
| 90/14833 | 12/1990 | WIPO . |

OTHER PUBLICATIONS

JP–A–64–40412, published Feb. 10, 1989.
JP–A–63–258807, published Oct. 26, 1988.
JP–A–2–502546 (WO 89/05642 derived from PCT/US88/04539), published Aug. 16, 1990.
Edward Sagarin, "Cosmetics Science and Technology", Interscience Publishers division of John Viley & Sons, New York, New York, third printing May 1966, pp. 115–117, 169, 169, 465, 466, 506, 507, 858–863, 1034, 1035, 1063–1070, 1111–1113, 1134, 1135 and 1155.
Susan Budavari, "The Merck Index", eleventh edition, published by Merck & Co., Inc., Rahway, N.J., 1989, pp. 1576, entry 9918.

*Primary Examiner*—James O. Wilson
*Attorney, Agent, or Firm*—Foley & Lardner

[57] ABSTRACT

An external skin treatment composition containing (I) vitamin A (retinol) and (II) as a stabilizer, a chelating agent/a polysaccharide, an oil, polyethylene (propylene) glycol, a hydroxy carboxylate, a neutral amino acid salt, an oil-soluble antioxidant/EDTA/a benzophenone compound, an oil-soluble antioxidant/an acid/a benzophenone compound, an inclusion compound of cyclodextrin including an antioxidant and/or an ultraviolet absorber, butanediol and/or an oil-soluble antioxidant, a water-soluble benzophenone compound, a basic amino acid and the salt thereof, an acidic amino acid and the salt thereof, a polar oil, a water-swellable clay mineral.

11 Claims, No Drawings

EXTERNAL SKIN TREATMENT COMPOSITION

This application is a division of application Ser. No. 08/204,286, filed Mar. 10, 1994 now U.S. Pat. No. 5,484,816 which is the national stage of PCT/JP93/00969 filed Jul. 13, 1993.

TECHNICAL FIELD

The present invention relates to an external skin treatment composition in which the stability of vitamin A is extremely improved.

BACKGROUND ART

It has been well known that vitamin A is effective for prevention or treatment of keratodermatitis and, prevention of and recovery from dermal aging.

Vitamin A, however, is structurally very unstable and can readily cause isomerization, decomposition, polymerization, etc., with light, air, heat, metal ion, etc. Thus, it has been difficult to stably formulate vitamin A into an external skin treatment composition.

SUMMARY OF THE INVENTION

Accordingly, the present invention relates to an external skin treatment composition in which the stability of vitamin A is extremely improved by formulating a stabilizer for improving the stability of vitamin A.

In accordance with the present invention, there is provided an external skin treatment composition comprising (I) vitamin A and (II) at least one stabilizer selected from the group consisting of (1) chelating agents and polysaccharides, (2) oils having an iodine value of 70 or more, (3) polyethylene glycol and/or polypropylene glycol, (4) hydroxy carboxylates, (5) neutral amino acids, (6) (i) at least one oil-soluble antioxidant selected from the group consisting of butyl hydroxytoluene, butyl hydroxyanisole, α,β,γ,δ-tocopherol, nordihydrogualaretin, propyl gallate, fatty acid esters of vitamin C and sorbic acid, (ii) at least one ethylenediaminetetraacetate and (iii) at least one benzophenone compound, (7) (i) at least one oil-soluble antioxidant selected from the group consisting of butyl hydroxytoluene, butyl hydroxyanisole, α,β,γ,δ-tocopherols, nordihydrogualaretin, propyl gallate and fatty acid esters of vitamin C, (ii) at least one compound selected from the group consisting of ascorbic acid, ascorbic acid salt, isoascorbic acid, isoascorbic acid salt, sorbic acid and sorbic acid salt and (iii) at least one benzophenone compound, (8) inclusion compounds of cyclodextrins including antioxidants and/or ultraviolet absorbers, (9) at least one kind of butanediol and/or at least one oil-soluble antioxidant, (10) at least one water-soluble benzophenone compound, (11) at least one compound selected from the group consisting of basic amino acids and the salts thereof, (12) at least one compound selected from the group consisting of acidic amino acids and the salts thereof, (13) at least one polar oil selected from the group consisting of pentaerythritol fatty acid esters and trimethylolpropane fatty acid esters, and (14) at least one water-swellable clay mineral.

BEST MODE FOR CARRYING OUT THE INVENTION

In consideration of the above circumstances, the present inventors have conducted extensive study and research efforts. As a result, it has been found that the stability of vitamin A is extremely improved by formulating the specified stabilizer therein. Thus the present invention has been achieved.

The present invention will be described in detail below.

As vitamin A used in the present invention, vitamin A (also called retinol), all-trans type vitamin A or 13-cis type vitamin A is desirable. A mixture thereof can also be used.

The amount of vitamin A to be formulated into the external skin treatment composition according to the present invention is not particularly limited. However, if the effect on the skin as a function of vitamin A is taking into consideration, the amount is 0.0001% by weight or more, based upon the total weight of the composition. If further effects of vitamin A are required, 0.001% by weight or more of the same is preferably used. The upper limit of the formulation amount is preferably 1% by weight in view of the properties as an external skin treatment composition.

According to the first embodiment of the present invention, as a stabilizer, the combination of a chelating agent and a polysaccharide is used.

As a chelating agent used in the present invention, mention may be made of inorganic alkali salts of ethylenediaminetetraacetate such as sodium salts and potassium salts thereof, organic alkali salts of ethylenediaminetetraacetate such as ethanolamines salts thereof (mono, di, tri and tetra salts), citric acid and inorganic alkali salts of citric acid such as sodium and potassium salts thereof, organic alkali salts of citric acid such as ethanolamine salts and basic amino acid salts thereof (mono, di, tri salts); metaphosphoric acid salts, polyphosphoric acid salts, tartaric acid salts.

The amount of a chelating agent to be formulated in accordance with the present invention is 0.001% by weight or more and the upper limit of the formulation amount cannot be particularly limited. However, when an extremely large amount of the agent is formulated, although the effects of the present invention are not impaired, crystals of the agent are possibly deposited or undesirable phenomena may occur, so that qualities as external skin treatment compositions cannot be maintained. The formulation amount is preferably 1% by weight or less.

As polysaccharides used in the present invention, mention may be made of cellulose, quinsseed, chondroitin sulfate, starch, galactan, dermatan sulfate, glycogen, gum arabic, heparan sulfate, hyaluronic acid, gum traganth, keratan sulfate, chondroitin, gum xanthane, mucoitin sulfate, guargum, dextran, keratosulfate, locust bean gum, succinoglucan, charonin, and the salts thereof.

The amount of polysaccharides to be formulated into the external skin treatment composition of the present invention is not particularly limited in view of the effects of the present invention. However, it is preferably 0.00001 to 5.0% by weight.

In the second embodiment of the present invention, as oils having an iodine value of 70 or more to be formulated as a stabilizer, typically, mention may be made of plant oils belonging to the drying oil group such as linseed oil, tung oil, soybean oil, sunflower oil, walnut oil, eno oil, evening primrose oil, cherrykernel oil and grape seed; plant oils belonging to the nondrying oil such as sesame oil, rape seed oil, cotton seed oil, rice bran oil and wheat embryo bud oil; avocado oil; olive oil; camellia oil; macadamia nut oil; fish oils such as sardine oil, mackerel oil, herring oil, cod-liver oil, oyster oil.

In these oils, iodine values are, for example, 168–190 in linseed oil, 114–138 in soybean oil, 122–150 in sunflower oil, 94–107 in rape seed oil, 90–121 in cotton seed oil, 75–90 in olive oil, 73–87 in camellia oil, 136–195 in sardine oil, 99–119 in herring oil.

Further, among free fatty acids and higher alcohols derived from these fats and oils, those having an iodine value of 70 or more include, for example, oleic acid, palmitic acid, linoleic acid, linolenic acid, eleostearic acid, γ-linolenic acid, arachidonic acid, eicosapentaene acid, oleyl alcohol.

One or more kinds of these oils are formulated into the composition. The formulation amount thereof for the purpose of exhibiting the effects of the present invention is preferably 0.01% by weight or more. Further, even if an excess amount of the same is formulated, the effects of the present invention are not impaired. However, if an extremely large amount of the same is formulated, qualities as external skin treatment compositions sometimes can be impaired. Thus caution should be taken not to impair the qualities. The formulation amount is particularly preferably 0.1 to 60% by weight.

According to the third embodiment of the present invention, as a stabilizer, one or two or more kinds of compounds selected from polyethylene glycol (PEG) and/or polypropylene glycol (PPG) are formulated.

As PEG, PPG to be formulated in accordance with the present invention, PEG200, PEG300, PEG400, PEG1500, PEG4000, PEG6000, PEG20000 as well as PPG400, PPG750, PPG1200, PPG2000, PPG3000 have been typically known.

One or more kinds of these compounds are formulated into the composition. The formulation amount thereof for the purpose of exhibiting the effects of the present invention is preferably 0.1% by weight or more. Further, even if an excess amount of the same is formulated, the effects of the present invention are not impaired. However, if an extremely large amount of the same is formulated, qualities as external skin treatment compositions sometimes can be impaired. Thus caution should be taken not to impair the qualities of the composition. The formulation amount is particularly preferably 1 to 80% by weight.

In the fourth embodiment of the present invention, as hydroxycarbonates included in the external skin treatment composition as a stabilizer, mention may be made of inorganic alkali salts such as sodium salts and potassium salts of citric acid, lactic acid, malic acid and tartaric acid, organic alkali salts such as ethanolamine salts and basic amino acid salts of citric acid, lactic acid, malic acid and tartaric acid (mono, di and tri salts are typically known).

One or two or more kinds thereof are included in the present composition. The formulation amount thereof for the purpose of exhibiting the effects of the present invention is preferably 0.001% by weight or more. Further, even if an excess amount of the same is formulated, the effects of the present invention are not impaired. However, if an extremely large amount of the same is formulated, qualities as external skin treatment compositions sometimes can be impaired. Thus caution should be taken not to impair the qualities of the composition. The formulation amount is particularly preferably 0.01 to 1% by weight.

In the fifth embodiment of the present invention, as neutral amino acids included in the external skin treatment composition as a stabilizer, mention may be made of glycine, alanine, seline, phenylalanine, proline and hydroxyproline.

One or two or more kinds thereof are included in the present composition. The formulation amount thereof for the purpose of exhibiting the effects of the present invention is preferably 0.001% by weight or more. Further, even if an excess amount of the same is formulated, the effects of the present invention are not impaired. However, if an extremely large amount of the same is formulated, the formulation amount exceeds individual solubility to possibly cause the precipitation of the crystals so that qualities as external skin treatment compositions sometimes can be impaired. Thus caution should be taken not to impair the qualities of the composition. The formulation amount is particularly preferably 0.01 to 10% by weight.

In the sixth embodiment of the present invention, as oil-soluble antioxidants included in the external skin treatment composition as a stabilizer, mention may be made of butyl hydroxytoluene (BHT), butyl hydroxyanisole (BHA), α,β,γ,δ-tocopherols, nordihydrogualaretin, propyl gallate, a fatty acid ester of vitamin C and sorbic acid.

An amount thereof to be formulated in accordance with the present invention is prefearbly 0.001% by weight or more, more preferably 0.01% by weight or more. In order to maintain the effects of the invention for a long time, the formulation amount is preferably 0.03% by weight. The upper limit of the formulation amount depends on the form of the external skin treatment composition and the formulation amount can be optionally selected. Thus, although the upper limit cannot be set, in view of the property of the external skin treatment composition, it is preferably 10% by weight or less.

As ethylenediaminetetraacetate used in the present invention, mention may be made of inorganic alkali salts such as sodium salts and potassium salts and organic alkali salts such as ethanolamines salts (mono, di, tri, tetra salts).

The formulation amount thereof is 0.001% by weight or more. The upper limit of the formulation amount cannot be particularly set. However, if an extremely large amount of the same is formulated, the effects of the present invention are not impaired, but crystals can be precipitated to impair the qualities of the external skin treatment composition. Thus the formulation amount is preferably 0.005 to 1% by weight.

As the benzophenone compound used in the present invention, mention may be made of 2,4-dihydroxybenzophenone (hereinafter referred to as benzophenone-1), 2,2',4,4,-tetrahydroxybenzophenone (hereinafter referred to as benzophenone-2), 2-hydroxy-4-methoxybenzophenone (hereinafter referred to as benzophenone-3), 2-hydroxy-4-methoxybenzophenone-5-sulfonic acid (hereinafter referred to as benzophenone-4), sodium 2-hydroxy-4-methoxybenzophenone-5-sulfonate (hereinafter referred to as benzophenone-5), 2,2'-dihydroxy-4,4'-dimethoxybenzophenone (hereinafre referred to as benzophenone-6), 2-hydroxy-5-chlorobenzophenone (hereinafter referred to as benzophenone-7), 2,2'-dihydroxy-4-methoxybenzophenone (hereinafter referred to as benzophenone-8), disodium 2,2 -dihydroxy-4,4'-dimethoxybenzophenone-5,5'-sulfonate (hereinafter referred to as benzophenone-9), 2-hydroxy-4-methoxy-4'-methylbenzophenone (hereinafter referred to as benzophenone-10) and 2-hydroxy-4-octyloxybenzophenone (hereinafter referred to as benzophenone-12).

The formulation amount thereof to the external skin treatment composition of the present invention is 0.001% by weight or more. The upper limit of the formulation amount cannot be particularly set. However, if an extremely large amount of the same is formulated, the effects of the present invention are not impaired, but crystals can be precipitated to impair the qualities of the external skin treatment composition. Thus the formulation amount is preferably 0.01 to 10% by weight.

In the seventh embodiment of the present invention, as a stabilizer, are formulated (A) at least one oil-soluble antioxidant selected from a group consisting of butyl hydroxytoluene (BHT), butyl hydroxyanisole (BHA), α,β,γ,δ-tocopherols, nordihydrogualaretin, propyl gallate and a fatty acid ester of vitamin C, (B) at least one compound selected from the group consisting of ascorbic acid, ascorbic acid salts, isoascorbic acid, isoascorbic acid salts, sorbic acid and sorbic acid salts, and (C) at least one benzophenone compound.

As oil-soluble antioxidants according to the present invention, mention may be made of BHT, BHA, α,β,γ,δ-tocopherols, nordihydrogualaretin, propyl gallate and a fatty acid ester of vitamin C.

An amount thereof to be formulated in accordance with the present invention is prefearbly 0.001% by weight or more, more preferably 0.01% by weight or more. In order to maintain the effects of the invention for a long time, the formulation amount is preferably 0.03% by weight. The upper limit of the formulation depends on the forms of the external skin treatment composition and the formulation can be optionally made. Thus, although the upper limit cannot be set, in view of the property of the external skin treatment composition, it is preferably 10% by weight.

As ascorbic acid (another name: vitamin C), isoascorbic acid (another name: erythorbic acid), sorbic acid and salts thereof, mention may be made of inorganic alkali salts such as sodium salts and potassium salts thereof as well as organic alkali salts such as ethanolamines salts and basic amino acids thereof. Particularly, ascorbic acid, sodium ascorbate, isoascorbic acid (another name: erythorbic acid), sodium isoascorbate (another name: sodium erythorbate), sorbic acid, sodium sorbate and potassium sorbate are preferably used.

In a system where each acid and a basic substance are co-utilized, a salt also can be formed.

An amount thereof to be formulated in accordance with the present invention is prefearbly 0.001% by weight or more. The upper limit of the formulation amount cannot particularly be set. However, if an extremely large amount of the same is formulated, the effects of the present invention are not impaired, but crystals can be precipitated to impair the qualities of the external skin treatment composition. Thus the formulation amount is preferably 10% by weight or less.

As the benzophenone compound used in the present invention, mention may be made of 2,4-dihydroxybenzophenone (hereinafter referred to as benzophenone-1), 2,2',4,4'-tetrahydroxybenzophenone (hereinafter referred to as benzophenone-2), 2-hydroxy-4-methoxybenzophenone (hereinafter referred to as benzophenone-3), 2-hydroxy-4-methoxybenzophenone-5-sulfonic acid (hereinafter referred to as benzophenone-4), sodium 2-hydroxy-4-methoxybenzophenone-5-sulfonate (hereinafter referred to as benzophenone-5), 2,2'-dihydroxy-4,4'-dimethoxybenzophenone (hereinafter referred to as benzophenone-6), 2-hydroxy-5-chlorobenzophenone (hereinafter referred to as benzophenone-7), 2,2'-dihydroxy-4-methoxybenzophenone (hereinafter referred to as benzophenone-8), disodium 2,2'-dihydroxy-4,4'-dimethoxybenzophenone-5,5'-sulfonate (hereinafter referred to as benzophenone-9), 2-hydroxy-4-methoxy-4'-methylbenzophenone (hereinafter referred to as benzophenone-10) and 2-hydroxy-4-octyloxybenzophenone (hereinafter referred to as benzophenone-12).

The formulation amount thereof to the external skin treatment composition of the present invention is 0.001% by weight or more. The upper limit of the formulation amount cannot be particularly set. However, if an extremely large amount of the same is formulated, the effects of the present invention are not impaired, but crystals can be precipitated to impair the qualities of the external skin treatment composition. Thus the formulation amount is preferably 10% by weight.

The cyclodextrin (CD) used in the present invention is cyclic oligosaccharides such as CD having the structure of α, β or γ due to the difference in glucose number (α-CD, β-CD, γ-CD); those to which a lower alkyl group is introduced, i.e., methyl CD (M-CD), ethyl CD (E-CD); hydroxyalkylated compounds, i.e., hydroxymethyl CD (HM-CD), hydroxyethyl CD (HE-CD), hydroxypropyl CD (HP-CD), hydroxybutyl CD (HB-CD).

Among these, α-CD and γ-CD have good solubility in water, but if they are produced according to a starch decomposition method, the yield of the product is low and therefore, this method is insufficient in view of the cost. β-CD is advantageous from the viewpoint of cost, but the solubility thereof is somewhat insufficient. In each case, if individual properties are well known and a compound is utilized on the basis of these well-known properties, the effects of the present invention can be sufficiently obtained.

In view of the frequent utilization thereof for external skin treatment compositions, due to their good solubility and low cost, methylated CD and hydroxylakylated CD are preferable, particularly, methyl-β-CD, hydroxyalkyl-β-CD are the most preferable.

The formulation amount of each CD to the external skin treatment composition of the present invention is 0.01% by weight or more. The upper limit of the formulation amount cannot be particularly limited by the effects of the present invention. However, if an extremely large amount of the same is formulated, the effects of the present invention are not impaired, but crystals can be precipitated to impair the qualities of the external skin treatment composition. Thus, the formulation amount of α-CD and γ-CD is preferably 10% by weight or less. While, regarding β-CD, 1% by weight or less and regarding lower alkylated CD, hydroxyalkylated CD, the amount is 30% by weight or less.

As oil-soluble antioxidants formulated into the external skin treatment composition according to the present invention, mention may be made of nordihydrogualaretin, BHT, BHA, α,β,γ,δ-tocopherols, propyl gallate, a fatty acid ester of vitamin C and sorbic acid. Among these, BHT, BHA, α,β,γ,δ-tocopherols are preferably used.

The formulation amount thereof used in the present invention is preferably 0.001% by weight or more, more preferably 0.01%.by weight or more. In order to maintain the effects of the invention for a long time, the formulation amount is preferably 0.03% by weight. The upper limit of the formulation depends on the form of the external skin treatment composition and the formulation can be optionally made. Thus, although the upper limit cannot be set, in view of the property of the external skin treatment composition, the antioxidant is preferably formulated in the amount of 1% by weight.

Examples of the ultraviolet absorber used in the present invention include benzophenone compounds represented by 2-hydroxy-4-methoxybenzophenone; cinnamic acid compounds represented by octylmethoxycinnamate, mono/di (methoxycinnamyl)-mono/dioctylglyceride; salicylic compounds represented by octylsalicylate; benzoic acid compounds represented by paraaminooctylbenzoate; dibenzoylmethane compounds represented by 4-t-butyl-4' methoxybenzoylmethane. Benzophenone compounds, cinnamic acid compounds and dibenzoylmethane compounds are preferably used.

The formulation amount thereof used in the present invention is preferably 0.001% by weight or more, more preferably 0.01% by weight or more. In order to maintain the effects of the invention for a long time, the formulation amount is preferably 0.03% by weight. The upper limit of the formulation depends on the form of the external skin treatment composition and the formulation can be optionally made. Thus, although the upper limit cannot be set, in view of the property of the external skin treatment composition, it is preferably 1% by weight.

A method for making antioxidants and ultraviolet absorbers to be included in the above-described CDs generally comprises the step of adding an antioxidant and an ultraviolet absorber to an aqueous solution of CDs (the concentration is 20 to 60% by weight) in an amount of 0.01 to 0.2 part on the basis of the amount of CD, then stirring the resulting mixture (50 to 3000 rpm) at a temperature of 20 to 60° C., whereby the inclusion compound can be obtained. It takes about 2 to 12 hours to obtain the same. The inclusion compound thus obtained is in a solubilized or emulsified state in an aqueous solution and can be used as it is as an external skin treatment composition. Alternatively, this solution can be lyophilized or spray-dried to form a powder.

Further, it is also possible to separately formulate CDs, an antioxidant and an ultraviolet absorber into an external skin treatment composition and to effect the inclusion of these compounds together therein.

In the ninth embodiment of the present invention, as butanediols to be formulated as a stabilizer, mention may be made of 1,2-butanediol, 1,3-butanediol, 1,4-butanediol.

One or more kinds thereof are included in accordance with the present invention. The formulation amount thereof for the purpose of exhibiting the effects of the present invention is preferably 0.01% by weight or more. Further, even if an excess amount of the same is formulated, the effects of the present invention are not impaired. However, if an extremely large amount of the same is formulated, qualities as external skin treatment compositions sometimes can be impaired. Thus the caution should be taken not to impair the qualities of the composition. The formulation amount is particularly preferably 0.1 to 40% by weight.

Examples of oil-soluble antioxidants to be formulated in accordance with the present invention include butyl hydroxytoluene (hereinafter, abbreviated as BHT), butyl hydroxyanisole (hereinafter, abbreviated as BHA), $\alpha,\beta,\gamma,\delta$-tocopherols, nordihydrogualaretin, propyl gallate and a fatty acid ester of vitamin C.

The formulation amount thereof is preferably 0.001% by weight or more, more preferably 0.005% by weight or more. In order to maintain the effects of the invention for a long time, the formulation amount is preferably 0.01% by weight or more. Although the upper limit of the formulation amount cannot be particularly set in view of the effects of the present invention, if an extremely large amount of the same is formulated, crystals can be precipitated so that the qualities as the external skin treatment composition sometimes can be impaired. Thus, caution should be taken so as not to impair the qualities of the composition. A preferable formulation amount is 10% by weight.

In the tenth embodiment of the present invention, as the water-soluble benzophenone compound used as a stabilizer, mention may be made of 2-hydroxy-4-methoxybenzophenone-5-sulfonic acid (hereinafter referred to as benzophenone-4) and the salt thereof, sodium 2-hydroxy-4-methoxybenzophenone-5-sulfonate (hereinafter referred to as benzophenone-5) and disodium 2,2'-dihydroxy-4,4'-dimethoxybenzophenone-5,5'-disulfonate (hereinafter referred to as benzophenone-9).

The formulation amount thereof to the external skin treatment composition of the present invention is preferably 0.001% by weight or more, particularly preferably 0.01% by weight or more. The upper limit of the formulation amount cannot be particularly set. However, if an extremely large amount of the same is formulated, the effects of the present invention are not impaired, but crystals can be precipitated to impair the qualities of the external skin treatment composition. Thus the formulation amount is preferably 5% by weight or less.

In the eleventh embodiment of the present invention, as a basic amino acid and the salt thereof to be formulated as a stabilizer, mention may be made of arginine, lysine, hydroxylysine, ornithine, and the hydrochloride, acetate, aspartate, pyrrolidone carboxylate thereof.

In addition to these, a basic amino acid and other acidic substances are co-utilized in the external skin treatment composition and a salt can be formed in situ.

One or more kinds of these compounds are formulated into the composition. The formulation amount thereof for the purpose of exhibiting the effects of the present invention is required to be 0.001% by weight or more. Further, even if an excess amount of the same is formulated, the effects of the present invention are not impaired. However, if an extremely large amount of the same is formulated, qualities as external skin treatment compositions sometimes can be impaired, for example, by precipitation of crystals. Thus, caution should be taken not to impair the qualities of the composition. The formulation amount is preferably 0.01 to 5% by weight.

The pH of the system is preferably 6 or more, more preferably 7 or more.

In the twelfth embodiment of the present invention, as an acidic amino acid and the salt thereof to be formulated as a stabilizer, mention may be made of acidic amino acids such as aspartic acid and glutamic acid, and inorganic alkali (sodium and potassium) salts thereof as well as organic alkali (ethanolamine and basic amino acids) salts thereof. Further, pyrrolidone carboxylic acid and the salt thereof also can be applied.

One or two or more kinds thereof are included in the present composition. The formulation amount thereof for the purpose of exhibiting the effects of the present invention is preferably 0.001% by weight or more, more preferably 0.01% by weight or more. Further, even if an excess amount of the same is formulated, the effects of the present invention are not impaired. However, if an extremely large amount of the same is formulated, the formulation amount exceeds individual solubility to possibly cause the precipitation of crystals so that qualities as external skin treatment compositions sometimes can be impaired. Thus, caution should be taken not to impair the qualities of the composition. The formulation amount is preferably 10% by weight or less.

In the thirteenth embodiment of the present invention, a polar oil used as a stabilizer is selected from a group consisting of pentaerythritol fatty acid ester preferably having 6 to 12 carbon atoms and trimethylolpropane fatty acid ester preferably having 6 to 12 carbon atoms. Examples thereof include pentaerythritol-tetra(2-ethylhexanoate), pentaerythritoltetracaprate, trimethylolpropane-tri(2-ethylhexanoate) and trimethylolpropane-tricaprate.

The amount thereof to be formulated in accordance with the present invention cannot be particularly limited because of the wide variety of utilization forms. However, if an extremely small amount of an oil is used, it cannot solubilize vitamin A or an oil-soluble antioxidant so that the effects of the present invention cannot be exhibited. Accordingly, an oil is desirably used in an amount over the total amount of vitamin A and an oil-soluble antioxidant to be formulated in the external skin treatment composition. The oil is preferably used in an amount of 0.002% by weight or more, more preferably 0.1% by weight or more. The upper limit of the formulation amount of the oil cannot be particularly set because of the wide variety of utilization forms. However, the upper limit can be determined by subtracting the sum of an oil-soluble antioxidant and vitamin A from the total amount of the external skin treatment composition.

Examples of oil-soluble antioxidants to be formulated into the external skin treatment composition in accordance with the present invention include BHT, BHA, $\alpha,\beta,\gamma,\delta$-tocopherols, nordihydrogualaretin, propyl gallate, a fatty acid ester of vitamin C and sorbic acid.

The formulation amount thereof used in the present invention is preferably 0.001% by weight or more, more preferably 0.01% by weight or more. In order to maintain the effects of the invention for a long time, the formulation amount is preferably 0.03% by weight.

The upper limit of the formulation depends on the forms of the external skin treatment composition and the formulation can be optionally determined. Thus, although the upper limit cannot be set, in view of the property of the external skin treatment composition, it is preferably 10% by weight.

In the fourteenth embodiment of the present invention, as a water-swellable clay mineral to be formulated as a stabilizer, mention may be made of, generally, a kind of colloidal water-containing aluminumsilicate. Specifical examples thereof include natural or synthetic smectite such as montmorillonite, bidelite, nontrolite, saponite, hectolite. As the commercially available products, mention may be made of Kunipia, Smectone (both are available from Kunimine Kogyo K.K.), Vegum (available from Vanderbilt K.K.), Laponite (available from Lapolt K.K.), Fluorotetrasilicon modified mica (available from Topee Kogyo K.K.). Further, synthetic mica known as sodium silicic mica and sodium or lithium teniolite also can be used.

The formulation amount thereof in the external skin treatment composition of the present invention is 0.01% by weight or more, preferably 0.1% or more. The upper limit of the formulation amount cannot be particularly set in view of the effects of the present invention. However, if an extremely large amount of the same is formulated, gelatin may be produced thus deteriorating the qualities of the external skin treatment composition. Thus, caution should be taken not to deteriorate the qualities of the composition. The formulation amount is preferably 50% by weight or less.

Examples of an antioxidant to be formulated in accordance with the present invention include butyl hydroxytoluene (hereinafter abbreviated as BHT), butyl hydroxyanisole (hereinafter abbreviated as BHA), nordihydrogualaretin, $\alpha,\beta,\gamma,\delta$-tocopherols, propyl gallate, vitamin C (ascorbic acid), erythorbic acid (isoascorbic acid), erythorbate, vitamin C fatty acid ester, sorbic acid and sorbic acid salt.

The formulation amount thereof used in the present invention is preferably 0.001% by weight or more, more preferably 0.01% by weight or more. In order to maintain the effects of the invention for a long time, the formulation amount is preferably 0.03% by weight.

The upper limit of the formulation amount depends on the forms of the external skin treatment composition and the formulation can be optionally determined. Thus, although the upper limit cannot be set, in view of the property of the external skin treatment composition, it is preferably 10% by weight.

Examples of the ultraviolet absorber used in the present invention include benzophenone compounds represented by 2-hydroxy-4-methoxybenzophenone, 2-hydroxy-4-methoxybenzophenone-5-sulfonic acid and 2,2'-dihydroxy-4,4'-dimethoxybenzophenone; cinnamic acid compounds represented by octylmethoxycinnamate, mono/di (methoxycinnamyl)-mono/dioctylglyceride; salicylic compounds represented by octylsalicylate; benzoic compounds represented by paraaminooctylbenzoate; benzoylmethane compounds represented by 4-t-butyl-4'-methoxybenzoylmethane.

One or more kinds thereof are formulated in the present composition. The formulation amount thereof for the purpose of exhibiting the effects of the present invention is preferably 0.001% by weight or more. Further, even if an excess amount of the same is formulated, the effects of the present invention are not impaired. However, if an extremely large amount of the same is formulated, qualities as external skin treatment compositions can sometimes be impaired. Thus, caution should be taken not to impair the qualities of the composition. The formulation amount is preferably 10% by weight or less.

As a chelating agent used in the present invention, mention may be made of inorganic alkali salts such as sodium salts and potassium salts of ethylenediaminetetraacetate, organic alkali salts such as ethanol amines salts of ethylenediaminetetraacetate (mono, di, tri and tetra salts), citric acid and inorganic alkali salts such as sodium and potassium salts of citric acid, organic alkali salts such as ethanol amine salts and basic amino acid salts of citric acid (mono, di, tri and tetra salts). Further, metaphosphoric acid salts or polyphosphoric acid salts can be used.

One or two or more kinds thereof are included in the present composition. The formulation amount thereof for the purpose of exhibiting the effects of the present invention is required to be 0.001% by weight or more. Further, even if an excess amount of the same is formulated, the effects of the present invention are not impaired. However, if an extremely large amount of the same is formulated, crystals can be precipitated so that the qualities as external skin treatment compositions can sometimes be impaired. Thus, caution should be taken not to impair the qualities of the composition. The formulation amount is preferably 1% by weight or less.

In addition to the above-described essential components, the external skin treatment composition according to the present invention can optionally contain a conventional base material of the external skin treatment composition usually used in cosmetics and quasi-drugs and other conventional components such as humectant, surfactant, preservative, water, alcohol, thickener, oil, drug, perfume, colorant, and ultraviolet absorber in an amount which does not deteriorate the effects of the present invention. The composition can be converted to liquid, gel, paste, cream, powder and solid form.

EXAMPLE

The present invention will be further described in more detail, by, but by no means limited to, the following Examples.

Production method and temperature test method of Examples 1-1, 1-2 and Comparative Examples 1-1, 1-2

Each oil component is completely dissolved at 60° C., and then has added thereto a solution of POE(10) oleyl ether, edetic acid salt, ethanol and dipropylene glycol dissolved in purified water, followed by cooling the resulting solution to 40° C. Thereafter, vitamin A is completely dissolved therein, and the solution is sealed in a brown glass sample tube. The tube is further wrapped with aluminum foil to completely cut light and is stored in a constant temperature bath at 40° C.

TABLE 1-1

Cosmetic oil formulation and vitamin A quantitative determination results (% by weight)

|  | Example 1-1 | Example 1-2 | Comp. Example 1-1 |
|---|---|---|---|
| Vitamin A | 0.01 | 0.02 | 0.01 |
| Disodium edetate | 0.001 | 0.005 | — |
| Hyaluronic acid | 0.001 | 0.001 | — |
| Purified water | 0.1 | 0.2 | — |
| Glycerol tri 2-ethylhexanoate triglyceride | balance | balance | balance |
| Isopropyl myristate | 10 | 35 | 10 |
| Squalane | 15 | 15 | 15 |
| Dipropylene glycol | 15 | 15 | 15 |
| Ethanol | 8 | 8 | 8 |
| POE(10) oleyl ether | 2 | 2 | 2 |
| Vitamin A quantitative determination value |  |  |  |
| Immediately after preparation (%) | 100 | 100 | 100 |
| After two weeks at 40° C. (%) | 93 | 98 | 56 |

In Examples 1-1 and 1-2, the stability of vitamin A is improved as compared with Comparative Example 1-1. This is the effect according to the present invention.

Quantitative determination method of vitamin A

According to the absorbance determination method at 325 nm using ethanol as a solvent, the quantitative determination was effected.

In the calculation, at the maximum absorption 325 nm, E (1%, 1 cm)=1835 was used.

TABLE 1-2

Emulsion formulation and vitamin A quantitative determination results (% by weight)

|  | Example 1-3 | Example 1-4 | Comp. Ex. 1-3 | Comp. Ex. 1-3 |
|---|---|---|---|---|
| Vitamin A | 0.03 | 0.001 | 0.03 | 0.001 |
| Disodium edetate | 0.01 | — | — | — |
| Trisodium citrate | 0.02 | 0.02 | — | — |
| Cetylisoocatnoate | 10 | 7 | 10 | 7 |
| Glycerol 2-ethylhexanoate | 2 | 4 | 2 | 4 |
| Squalane | 2 | 2 | 2 | 2 |
| Cetyl alcohol | 2 | 2 | 2 | 2 |
| Vaseline | 1 | 1 | 1 | 1 |
| Glyceryl monostearate | 1.5 | 1.5 | 1.5 | 1.5 |
| POE(60) hardened castor oil | 1.3 | 1.3 | 1.3 | 1.3 |
| Carboxyvinyl polymer | 0.2 | 0.3 | 0.2 | 0.3 |
| Gum xanthane | 0.05 | 0.1 | — | — |
| Caustic potash | 0.06 | 0.08 | 0.06 | 0.08 |
| Glycerol | 10 | 10 | 10 | 10 |

TABLE 1-2-continued

Emulsion formulation and vitamin A quantitative determination results (% by weight)

|  | Example 1-3 | Example 1-4 | Comp. Ex. 1-3 | Comp. Ex. 1-3 |
|---|---|---|---|---|
| Propylene glycol | 3 | 3 | 3 | 3 |
| Ethyl paraben | 0.2 | 0.2 | 0.2 | 0.2 |
| Purified water | To total amount 100 | | | |
| Vitamin A quantitative determination value |  |  |  |  |
| Immediately after preparation (%) | 100 | 100 | 100 | 100 |
| After one month at 40° C. (%) | 95 | 97 | 31 | 38 |

In Examples 1-3 and 1-4, the stability of vitamin A is improved as compared with Comparative Example. This is the effect according to the present invention.

TABLE 1-3

Cosmetic lotion and vitamin A quantitative determination results (% by weight)

|  | Example 1-5 | Example 1-6 | Example 1-7 | Comp. Ex. 1-4 |
|---|---|---|---|---|
| Disodium edetate | 0.5 | — | 0.05 | — |
| Tetrapotassium edetate | — | 0.3 | 0.05 | — |
| Sodium hyaluronate | 0.1 | 0.05 | — | — |
| Soium chondroitin sulfate | — | — | 0.2 | — |
| Ethanol | 5.0 | 5.0 | 5.0 | 5.0 |
| Methyl paraben | 0.1 | 0.1 | 0.1 | 0.1 |
| Vitamin A | 0.0001 | 0.0001 | 0.0001 | 0.0001 |
| Octadodecanol | 0.001 | 0.001 | 0.001 | 0.001 |
| POE(60) hardened castor oil | 0.4 | 0.4 | 0.4 | 0.4 |
| Lactic acid | 0.01 | 0.01 | 0.01 | 0.01 |
| Sodium lactate | 0.1 | 0.1 | 0.1 | 0.1 |
| Glycerol | 2.0 | 2.0 | 2.0 | 2.0 |
| Purified water | To total amount 100 | | | |
| Vitamin A quantitative determination value |  |  |  |  |
| Immediately after preparation (%) | 100 | 100 | 100 | 100 |
| After two weeks at 40° C. (%) | 95 | 93 | 91 | 49 |

In Examples 1-5, 1-6, and 1-7, the stability of vitamin A is improved as compared with Comparative Example. This is the effect according to the present invention.

| Example 1-8: Cosmetic lotion | (% by weight) |
|---|---|
| Oleyl alcohol | 0.005 |
| Vitamin A | 0.0001 |
| POE(50) oleyl ether | 0.7 |
| Trisodium edetate | 1 |
| Lactic acid | 0.01 |
| Sodium lactate | 0.09 |
| Soium chondroitin sulfate | 0.1 |
| Ethanol | 8 |
| Glycerol | 2 |
| Methyl paraben | 0.2 |
| Purified water | To total amount 100 |

| Example 1-9: Cream | (% by weight) |
|---|---|
| Squalane | 15 |
| Glycerol tri 2-ethylhexanoate | 8 |

| Example 1-9: Cream | (% by weight) |
| --- | --- |
| Isopropylmyristate | 7 |
| Vitamin A | 0.3 |
| Vaseline | 2 |
| Butyl paraben | 0.1 |
| Propyl paraben | 0.1 |
| Glycerol monooleate | 3 |
| Diglyceroldiisostearate | 2 |
| PEG400 dioleate | 1 |
| Glycerol | 10 |
| Cellulose powder | 1 |
| Dipropylene glycol | 5 |
| Disodium edetate | 0.01 |
| Triethanolamine | 0.02 |
| Purified water | To total amount 100 |

| Example 1-10: Oilessence | (% by weight) |
| --- | --- |
| Glycerol tri 2-ethylhexanoate | 50 |
| Octyldodecanol | 20 |
| Squalane | 10 |
| Vitamin A | 1 |
| Dibutylphthalate | 9 |
| Ethyl alcohol | 9.989 |
| Cellulose powder | 0.01 |
| Sodium edetate | 0.001 |

| Example 1-11: Oil gel | (% by weight) |
| --- | --- |
| Glycerol tri 2-ethylhexanoate | 60 |
| POE(20) octyldodecylether | 16 |
| Vitamin A | 0.1 |
| Glycerol | 16 |
| Sodium hyaluronate | 0.01 |
| Disodium edetate | 0.05 |
| Purified water | To total amount 100 |

| Example 1-12: Cream | (% by weight) |
| --- | --- |
| Cetostearyl alcohol | 3.5 |
| Squalane | 30.0 |
| Beeswax | 3.0 |
| Reduced lanolin | 5.0 |
| Ethyl paraben | 0.3 |
| POE(50) oleyl alcohol ether | 2.0 |
| Glycerol monostearate | 2.0 |
| Diethanol amine edetate | 0.01 |
| Perfume | 0.03 |
| Vitamin A | 0.0001 |
| Dermatan sulfate | 0.1 |
| Glycerol | 15.0 |
| Purified water | balance |

| Example 1-13: Pack | (% by weight) |
| --- | --- |
| Gum xanthane | 1.0 |
| Polyvinyl alcohol | 10.0 |
| Propylene glycol | 7.0 |
| Ethanol | 10.0 |
| Vitamin A | 0.01 |
| Monosodium edetate | 0.1 |
| Methyl paraben | 0.05 |
| POE(60) hydrogenated castor oil | 0.2 |
| Perfume | 0.05 |
| Purified water | balance |

| Example 1-14: Compact face powder | (% by weight) |
| --- | --- |
| Vitamin A | 0.0005 |
| Talc | 85.4 |
| Stearic acid | 2.5 |
| Squalane | 3.5 |
| Sorbitansesquioleate | 1.8 |
| Triethanolamine | 1.2 |
| Quinsseed | 0.001 |
| Salt of edetic acid | 0.001 |
| Pigment | q.s. |
| Perfume | q.s. |

| Example 1-15: Lipstick | (% by weight) |
| --- | --- |
| Vitamin A | 0.00001 |
| Microcrystalline wax | 3.0 |
| Bees wax | 3.0 |
| Ceresin wax | 5.0 |
| Liquid paraffin | 19.0 |
| Squalane | 20.0 |
| Carnauba wax | 3.0 |
| Candellira wax | 3.0 |
| Gum arabic | 0.01 |
| Monosodium salt of edetic acid | 0.01 |
| Color controlling colorant | 7.0 |
| Dibutylhydroxytoluene | 0.05 |
| Perfume | q.s. |
| Lanolin | balance |

| Example 1-16: Emulsion | (% by weight) |
| --- | --- |
| Vitamin A | 1.0 |
| Hyaluronic acid | 0.1 |
| Tetraethanol amine edetate | 1.0 |
| Ethanol | 2.0 |
| Glycerol | 10.0 |
| Propylene glycol | 3.0 |
| Carboxyvinyl polymer | 0.3 |
| KOH | 0.1 |
| Methyl paraben | 0.1 |
| Cetanol | 2.5 |
| Vaseline | 2.0 |
| Squalane | 10.0 |
| Isopropyl myristate | 5.0 |
| Glycerylmonostearate | 2.0 |
| POE(25) Cetyl ether | 2.0 |
| Purified water | balance |

| Example 1-17: Emulsion | (% by weight) |
| --- | --- |
| Vitamin A | 0.3 |
| Chondroitin sulfate | 0.01 |
| Trisodium citrate | 0.1 |
| Ethanol | 5.0 |

-continued

| Example 1-17: Emulsion | (% by weight) |
|---|---|
| Glycerol | 5.0 |
| Propylene glycol | 5.0 |
| Carboxyvinyl polymer | 0.2 |
| KOH | 0.06 |
| Methyl paraben | 0.2 |
| POE(60) Hydrogenated castor oil | 1.0 |
| Squalane | 3.0 |
| Isopropyl myristate | 3.0 |
| Purified water | balance |

The external skin treatment compositions of Examples 1-8 to 1-17 were excellent in the stability of vitamin A in daily use.

As described hereinabove, in the external skin treatment composition of the present invention, by formulating one or more chelating agents and polysaccharides such as hyaluronic acid and chondroitin sulfate, the stability of vitamin A can be extremely improved Example 2-1 to 2-3 and Comparative Example 2-1 to 2-2

TABLE 2-1

Vitamin A stability determination results in various oils (% by weight)

| | Example 2-1 | Example 2-2 | Example 2-3 | Comp. Example 2-1 | Comp. Example 2-2 |
|---|---|---|---|---|---|
| Olive oil (IV = 75) | 99 | — | — | — | — |
| Cotton seed oil (IV = 95) | — | 99 | — | — | — |
| Evening primrose Oil (IV = 190) | — | — | 50 | — | — |
| Squalane (IV = 1) | — | — | 49 | 49 | 99 |
| Palm oil (IV = 12) | — | — | — | 50 | — |
| Vitamin A | 1 | 1 | 1 | 1 | 1 |
| Quantitative determination value of vitamin A | | | | | |
| Immediately after preparation (%) | 100 | 100 | 100 | 100 | 100 |
| After ten days at 50° C. (%) | 93 | 98 | 97 | 58 | 39 |

In Examples 2-1, 2-2 and 2-3, the stability of vitamin A is improved as compared with Comparative Example. This is the effect according to the present invention.

Quantitative determination method of vitamin A

According to the absorbance determination method at 325 nm using ethanol as a solvent, the quantitative determination was effected.

In the calculation, at the maximum absorption 325 nm, E (1%, 1 cm)=1835 was used.

| Example 2-4: Cream | (% by weight) |
|---|---|
| Cetanol | 3 |
| Glycerylmonostearate | 2 |
| POE(25) Cetyl ether | 1 |
| Stearic acid | 3 |
| Vaseline | 3 |
| Olive oil (IV = 80) | 3 |
| Cotton seed oil (IV = 100) | 1 |
| Squalane | 5 |
| Vitamin A | 0.1 |
| BHT | 0.05 |
| Perfume | q.s. |
| Propylene glycol | 3 |
| Potassium hydroxide | 0.2 |
| Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 2-5: Lipstick | (% by weight) |
|---|---|
| Solid paraffin | 8 |
| Carnauba wax | 4 |
| Candellira wax | 4 |
| Microcrystalline wax | 6 |
| Hydrogenated lanolin | 15 |
| Castor oil (IV = 85) | 46.7 |
| Oyster oil (IV = 160) | 5 |
| Evening primrose oil (IV = 190) | 3 |
| Vitamin A | 1 |
| BHT | 0.3 |
| Mixed colorant (red type) | 7 |
| Perfume | q.s. |

Each of the above-described starting materials is thermally melted at 80° C., and thereafter, the molten product is poured into a given container to obtain a lipstick.

| Example 2-6: Cosmetic lotion | (% by weight) |
|---|---|
| Vitamin A | 0.0001 |
| Oleyl alcohol (IV = 80) | 0.01 |
| α-tocopherol | 0.005 |
| POE(20) Octyldodecanol | 0.8 |
| Ethanol | 8 |
| Propylene glycol | 3 |
| Glycerol | 1 |
| Methyl paraben | 0.15 |
| Lactic acid | 0.01 |
| Sodium lactate | 0.09 |
| Purified water | To total amount 100 |

| Example 2-7: Eye wrinkle oil | (% by weight) |
|---|---|
| Macadamia nut oil (IV = 75) | 40 |
| Glycerol tri γ-linolenate (IV = 198) | 1 |
| Glycerol tri 2-ethylhexanoate | 25 |
| Sunflower oil (IV = 130) | 20 |
| Squalane | 10 |
| PEG600 dioleate | 2.8 |
| δ-tocopherol | 1 |
| Vitamin A | 0.2 |

| Example 2-8: Night cream | (% by weight) |
| --- | --- |
| Olive oil (IV = 80) | 8 |
| Evening primrose oil (IV = 185) | 2 |
| Squalane | 20 |
| PEG400 diisostearate | 1 |
| Diglycerol dioleate | 1 |
| Butyl paraben | 0.15 |
| Glycerol monoleate | 2 |
| Vitamin A | 0.25 |
| Glycerol | 10 |
| Magnesium sulfate | 0.2 |
| Purified water | To total amount 100 |

The external skin treatment compositions of Examples 2-4 to 2-8 were excellent in the stability of vitamin A in daily use.

As described hereinabove, in the external skin treatment composition of the present invention, by formulating an oil having an iodine value of 70 or more, the stability of vitamin A can be extremely improved.

Example 3-1 to 3-3 and Comparative Example 3-1 to 3-2

TABLE 3-1

Vitamin A stability determination results in various bases (% by weight)

|  | Example 3-1 | Example 3-2 | Example 3-3 | Comp. Example 3-1 | Comp. Example 3-2 |
| --- | --- | --- | --- | --- | --- |
| PEG400 | 99.9 | — | — | — | — |
| PEG1500 | — | 99.9 | — | — | — |
| PPG1200 | — | — | 50 | — | — |
| Propylene glycol | — | — | 49.9 | 29.9 | — |
| Squalane | — | — | — | 70 | 99.9 |
| Vitamin A | 0.1 | 0.1 | 0.1 | 0.1 | 0.1 |
| Quantitative determination result of vitamin A | | | | | |
| Immediately after preparation (%) | 100 | 100 | 100 | 100 | 100 |
| After five days at 50° C. (%) | 92 | 93 | 90 | 58 | 39 |

In Examples 3-1, 3-2 and 3-3, the stability of vitamin A is improved as compared with the Comparative Example. This is the effect according to the present invention.

Quantitative determination method of vitamin A

According to the absorbance determination method at 325 nm using ethanol as a solvent, the quantitative determination was effected.

In the calculation, at the maximum absorption 325 nm, E (1%, 1 cm)=1835 was used.

| Example 3-4: Cream | (% by weight) |
| --- | --- |
| A. Cetanol | 3 |
| Glyceryl monostearate | 2 |
| POE(25) Cetyl ether | 1 |
| Stearic acid | 3 |
| Vaseline | 3 |
| Isopropyl myristate | 5 |
| Squalane | 5 |
| Vitamin A | 0.1 |
| BHT | 0.05 |
| Perfume | q.s. |

-continued

| Example 3-4: Cream | (% by weight) |
| --- | --- |
| PEG1500 | 3 |
| Glycerol | 9 |
| Potassium hydroxide | 0.2 |
| Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 3-5: Lipstick | (% by weight) |
| --- | --- |
| Solid paraffin | 8 |
| Carnauba wax | 2 |
| Candelilla wax | 4 |
| Microcrystalline wax | 6 |
| Hydrogenated lanolin | 15 |
| Isopropyl myristate | To total amount 100 |
| Glyceryl diisostearate | 30 |
| PPG3000 | 15 |
| Vitamin A | 1 |
| BHT | 0.3 |
| Mixed colorant (red type) | 7 |
| Perfume | q.s. |

Each of the above-described starting materials is thermally melted at 80° C., and thereafter, the molten product is poured into a given container to obtain a lipstick.

| Example 3-6: Cosmetic lotion | (% by weight) |
| --- | --- |
| Vitamin A | 0.0001 |
| Oleyl alcohol | 0.001 |
| α-tocopherol | 0.005 |
| POE(20) Octyldodecanol | 0.8 |
| Ethanol | 8 |
| PEG300 | 3 |
| PEG1500 | 1 |
| Methyl paraben | 0.15 |
| Lactic acid | 0.03 |
| Sodium lactate | 0.07 |
| Purified water | To total amount 100 |

| Example 3-7: Eye wrinkle oil | (% by weight) |
| --- | --- |
| Olive oil | 40 |
| Glycerol tri 2-ethylhexanoate | 26 |
| Squalane | 30 |
| PPG4000 | 2 |
| PEG20000 | 0.9 |
| δ-tocopherol | 1 |
| Vitamin A | 0.1 |

| Example 3-8: Beauty paste | (% by weight) |
| --- | --- |
| PEG300 | 30 |
| PEG1500 | 40 |
| PEG4000 | 10 |
| Vitamin A | 0.3 |
| Isopropyl myristate | 5 |

-continued

| Example 3-8: Beauty paste | (% by weight) |
|---|---|
| POE(25) Cetyl ether | 2 |
| Stearic acid | 5 |
| Purified water | To total amount 100 |

| Example 3-9: Night cream | (% by weight) |
|---|---|
| Squalane | 15 |
| Isopropyl myristate | 5 |
| Silicon dioxide | 3 |
| Vaseline | 6 |
| Glyceryl monoisostearate | 2 |
| POE(7) Hydrogenated castor oil | 1.5 |
| Propyl paraben | 0.2 |
| Vitamin A | 0.4 |
| PEG6000 | 3 |
| PEG400 | 3 |
| Glycerol | 17 |
| Purified water | To total amount 100 |

The external skin treatment compositions of Examples 3-4 to 3-9 were excellent in the stability of vitamin A in daily use.

As described hereinabove, in the external skin treatment composition of the present invention, by formulating polyethylene glycol and/or propylene glycol, the stability of vitamin A can be extremely improved.

Examples 4-1 to 4-3 and Comparative Example 4-1

TABLE 4-1

Vitamin A stability determination results in emulsion (% by weight)

|  | Example 4-1 | Example 4-2 | Example 4-3 | Comp. Example 4-1 |
|---|---|---|---|---|
| Purified water | To toal amount 100 | | | |
| Glycerol | 10 | 10 | 10 | 10 |
| Carboxyvinyl polymer | 0.2 | 0.2 | 0.2 | 0.2 |
| Caustic potash | 0.03 | 0.03 | 0.06 | 0.06 |
| Ethyl alcohol | 5 | 5 | 5 | 5 |
| Methyl paraben | 0.1 | 0.1 | 0.1 | 0.1 |
| Cetyl alcohol | 2 | 2 | 2 | 2 |
| Vaseline | 3 | 3 | 3 | 3 |
| Squalane | 5 | 5 | 5 | 5 |
| Isopropyl myristate | 4 | 4 | 4 | 4 |
| Glyceryl monostearate | 1.5 | 1.5 | 1.5 | 1.5 |
| POE(60) Hydrogenated castor oil | 2 | 2 | 2 | 2 |
| Trisodium citrate | 0.08 | — | 0.04 | — |
| Sodium lactate | — | 0.09 | 0.05 | — |
| Vitamin A | 0.3 | 0.3 | 0.3 | 0.3 |
| Quantitative determination value of vitamin A | | | | |
| Immediately after preparation (%) | 100 | 100 | 100 | 100 |
| After two weeks at 40° C. (%) | 98 | 93 | 95 | 75 |

In Examples 4-1, 4-2 and 4-3, the stability of vitamin A is improved as compared with the Comparative Example. This is the effect according to the present invention.

Quantitative determination method of vitamin A

According to the absorbance determination method at 325 nm using ethanol as a slovent, the quantitative determination was effected.

In the calculation, at the maximum abosrption 325 nm, E (1%, 1 cm)=1835 was used.

| Example 4-4: Cream | (% by weight) |
|---|---|
| A. Cetanol | 3 |
| Glycerylmonostearate | 2 |
| POE(25) Cetyl ether | 1 |
| Stearic acid | 3 |
| Vaseline | 3 |
| Olive Oil | 3 |
| Isopropyl palmitate | 1 |
| Squalane | 5 |
| Vitamin A | 0.1 |
| BHT | 0.05 |
| Perfume | q.s. |
| B. Propylene glycol | 3 |
| Potassium hydroxide | 0.2 |
| Trisodium citrate | 1 |
| Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 4-5: Beauty essence | (% by weight) |
|---|---|
| Carboxyvinyl polymer | 0.4 |
| Glycerol | 5 |
| Propylene glycol | 5 |
| Sodium lactate | 0.05 |
| Triethanolamine | 3.8 |
| POE(60) Hydrogenated castor oil | 0.5 |
| Vitamin A | 0.1 |
| Squalane | 1 |
| α-tocopherol | 0.05 |
| Methyl paraben | 0.2 |
| Ethyl alcohol | 6 |
| Purified water | To total amount 100 |

| Example 4-6: Cosmetic lotion | (% by weight) |
|---|---|
| Glycerol | 2 |
| Ethanol | 7 |
| POE(50) Oleyl ether | 0.5 |
| Oleyl alcohol | 0.002 |
| Vitamin A | 0.0001 |
| Trisodium citrate | 0.1 |
| Methyl paraben | 0.1 |
| Purified water | To total amount 100 |

| Example 4-7: Oil gel | (% by weight) |
|---|---|
| Vitamin A | 1 |
| Glycerol tri 2-ethylhexanoate | 40 |
| Olive oil | 10 |
| BHT | 0.1 |
| BHA | 0.05 |
| POE(20) Octyldodecyl ether | 16 |
| Glycerol | 15 |
| Disodium citrate | 0.1 |
| Purified water | To total amount 100 |

| Example 4-8: Night Cream | (% by weight) |
|---|---|
| Squalane | 15 |
| Glycerol tri 2-ethylhexanoate | 5 |
| Vaseline | 5 |
| Butyl paraben | 0.2 |
| Diglycerol diisostearate | 2 |
| PEG400 Diisostearate | 0.5 |
| Vitamin A | 0.1 |
| Glycerol | 10 |
| Trisodium citrate | 0.3 |
| Sodium lactate | 0.1 |
| Lactic acid | 0.1 |
| Purified water | To total amount 100 |

The external skin treatment compositions of Examples 4-4 to 4-8 were excellent in the stability of vitamin A in daily use.

As described hereinabove, in the external skin treatment composition of the present invention, by formulating hydroxycarboxylate, the stability of vitamin A can be extremely improved.

Examples 5-1 to 5-3 and Comparative Example 5-1

TABLE 5-1

Vitamin A stability determination results in emulsion (% by weight)

|  | Example 5-1 | Example 5-2 | Example 5-3 | Comp. Example 5-1 |
|---|---|---|---|---|
| Purified water | To total amount 100 | | | |
| Glycerol | 10 | 10 | 10 | 10 |
| Carboxyvinyl polymer | 0.2 | 0.2 | 0.2 | 0.2 |
| Caustic potash | 0.06 | 0.06 | 0.06 | 0.06 |
| Ethyl alcohol | 5 | 5 | 5 | 5 |
| Methyl paraben | 0.1 | 0.1 | 0.1 | 0.1 |
| Cetyl alcohol | 2 | 2 | 2 | 2 |
| Butyl alcohol | 1 | 1 | 1 | 1 |
| Vaseline | 3 | 3 | 3 | 3 |
| Squalane | 5 | 5 | 5 | 5 |
| Isopropyl myristate | 4 | 4 | 4 | 4 |
| Glyceryl monostearate | 1.5 | 1.5 | 1.5 | 1.5 |
| POE(60) Hydrogenated castor oil | 2 | 2 | 2 | 2 |
| BHT | 0.03 | 0.03 | 0.03 | 0.03 |
| Glycine | 1 | — | — | — |
| Hydroxy proline | 1 | 0.5 | 0.01 | — |
| Vitamin A | 0.3 | 0.3 | 0.3 | 0.3 |
| Quantitative determination result of vitamin A | | | | |
| Immediately after preparation (%) | 100 | 100 | 100 | 100 |
| After two weeks at 40° C. (%) | 98 | 96 | 88 | 55 |

In Examples 5-1, 5-2 and 5-3, the stability of vitamin A is improved as compared with the Comparative Example. This is the effect according to the present invention.

Quantitative determination method of vitamin A

According to the absorbance determination method at 325 nm using ethanol as a solvent, the quantitative determination was effected.

In the calculation, at the maximum absorption 325 nm, E (1%, 1 cm)=1835 was used.

| Example 5-4: Cream | | (% by weight) |
|---|---|---|
| A. | Cetanol | 3 |
| | Glyceryl monostearate | 2 |
| | POE(25) Cetyl ether | 1 |
| | Stearic acid | 3 |
| | Vaseline | 3 |
| | Olive oil | 3 |
| | Isopropyl myristate | 1 |
| | Squalane | 5 |
| | Vitamin A | 0.1 |
| | BHT | 0.5 |
| | Perfume | q.s. |
| B. | Propylene glycol | 3 |
| | Potassium hydroxide | 0.2 |
| | Alanine | 5 |
| | Hydroxy proline | 5 |
| | Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 5-5: Beauty essence | (% by weight) |
|---|---|
| Carboxyvinyl polymer | 0.4 |
| Glycerol | 5 |
| Propylene glycol | 5 |
| Alanine | 1 |
| Triethanolamine | 3.4 |
| POE(60) Hydrogenated castor oil | 0.5 |
| Vitamin A | 0.1 |
| Squalane | 1 |
| α-tocopherol | 1 |
| Methyl paraben | 0.2 |
| Ethyl alcohol | 6 |
| Purified water | To total amount 100 |

| Example 5-6: Cosmetic lotion | (% by weight) |
|---|---|
| Glycerol | 2 |
| Ethanol | 7 |
| POE(50) Oleyl ether | 0.5 |
| Oleyl alcohol | 0.002 |
| Vitamin A | 0.0001 |
| Serine | 0.3 |
| Leucine | 0.1 |
| Lactic acid | 0.02 |
| Sodium lactate | 0.07 |
| Methyl paraben | 0.1 |
| Purified water | To total amount 100 |

| Example 5-7: Oil gel | (% by weight) |
|---|---|
| Vitamin A | 1 |
| Glycerol tri 2-ethylhexanoate | 40 |
| Olive oil | 10 |
| BHT | 0.2 |
| BHA | 0.05 |
| POE(20) Octyldodecyl ether | 16 |
| Glycerol | 15 |
| Glycine | 0.1 |
| Purified water | To total amount 100 |

| Example 5-8: Night cream | (% by weight) |
| --- | --- |
| Liquid paraffin | 15 |
| Glycerol tri 2-ethylhexanoate | 7 |
| Vaseline | 6 |
| Solid paraffin | 2 |
| Diglycerol dioleate | 1.5 |
| Triglycerol diisosearate | 1.5 |
| Vitamin A | 0.1 |
| Propyl paraben | 0.2 |
| Propylene glycol | 4 |
| Glycerol | 15 |
| Glycine | 1 |
| Hydroxyproline | 1 |
| Purified water | To total amount 100 |

The external skin treatment compositions of Examples 5-4 to 5-8 were excellent in the stability of vitamin A in daily use.

As described hereinabove, in the external skin treatment composition of the present invention, by formulating, a neutral amino acid, the stability of vitamin A can be extremely improved.

Example 6-1 to 6-2 and Comparative Example 6-1 to 6-2

TABLE 6-1

Cosmetic oil formulation and vitamin A. quantitative determination results (% by weight)

| | Example 6-1 | Example 6-2 | Comp. Example 6-1 | Comp. Example 6-2 |
| --- | --- | --- | --- | --- |
| Vitamin A | 0.01 | 0.2 | 0.01 | 0.2 |
| BHT | 0.005 | 0.03 | 0.005 | 0.03 |
| dl-α-tocopherol | — | 0.01 | — | 0.01 |
| Benzophenone-3 | 0.05 | 0.1 | — | — |
| Octylmethoxycinnamate | — | — | 0.05 | 0.1 |
| Disodium edetate | 0.001 | 0.005 | — | 0.005 |
| Purified water | 0.1 | 0.2 | — | 0.2 |
| Glycerol tri 2-ethylhexanoate | 45 | 20 | 45 | 20 |
| Isopropyl myristate | 10 | 35 | 10 | 35 |
| Squalane | 24.834 | 24.455 | 24.935 | 24.455 |
| Dipropylene glycol | 10 | 10 | 10 | 10 |
| Ethanol | 8 | 8 | 8 | 8 |
| POE(10) Oleyl ether | 2 | 2 | 2 | 2 |
| Vitamin A quantitative determination value | | | | |
| Immediately after preparation (%) | 100 | 100 | 100 | 100 |
| After two months at 40° C. (%) | 93 | 98 | 68 | 82 |

In Examples 6-1 and 6-2, the stability of vitamin A is improved as compared with Comparative Example. This is the effect according to the present invention.

Production method and temperature test method of Examples 6-1, 6-2 and Comparative Examples 6-1, 6-2

BHT, tocopherol, benzophenone and octylmethoxycinnamate are each completely dissolved in oil at 60° C., then to the resulting solution is added a solution of edetate, ethyl alcohol and dipropylene glycol dissolved in purified water, followed by cooling the resulting solution to 40° C. Thereafter, vitamin A is completely dissolved therein, and the solution is sealed in a brown glass sample tube. The tube is further wrapped with aluminum foil to completely cut light and is stored in a constant temperature bath at 40° C.

Quantitative determination method of vitamin A

According to the absorbance determination method at 325 nm using ethanol as a solvent, the quantitative determination was effected.

In the calculation, at the maximum absorption 325 nm, E (1%, 1 cm)=1835 was used.

Production method and temperature test method of Examples 6-3. 6-4 and Comparative Examples 6-3, 6-4

BHT, tocopherol and benzophenone-2 are each completely dissolved in oil and a surfactant at 70° C., and thereafter, immediately before emulsification, vitamin A is completely dissolved therein to form an oil phase.

Glycerol, propylene glycol, carboxyvinyl polymer, caustic potash, trisodium edetate and benzophenone-5 are completely dissolved in purified water. The oil phase is added to the resulting aqueous phase heated to 70° C., then the mixture obtained is emulsified by a homomixer type emulsifier. Then the resulting product is subjected to a cooling treatment by a heat exchanger to 30° C. to form an emulsion.

The emulsion is filled in a glass bottle having a metal coat applied thereto, tightly sealed and is stored in a constant temperature bath at 40° C.

TABLE 6-2

Emulsion formulation and vitamin A quantitative determination results (% by weight)

| | Example 6-3 | Example 6-4 | Comp. Example 6-3 | Comp. Example 6-4 |
| --- | --- | --- | --- | --- |
| Vitamin A | 0.3 | 0.01 | 0.3 | 0.01 |
| BHT | 0.05 | 0.01 | 0.05 | 0.01 |
| di-α-tocopherol | 0.01 | 0.02 | 0.01 | 0.02 |
| Trisodium edetate | 0.02 | 0.02 | 0.02 | — |
| Benzophenone-2 | 0.1 | 0.05 | — | 0.02 |
| Benzophenone-5 | — | 0.05 | — | — |
| Cetylisooctanoate | 10 | 7 | 10 | 7 |
| Isopropyl myristate | 2 | 4 | 2 | 4 |
| Squalane | 2 | 2 | 2 | 2 |
| Cetyl alcohol | 2 | 2 | 2 | 2 |
| Vaseline | 1 | 1 | 1 | 1 |
| Glyceryl monostearate | 1.5 | 1.5 | 1.5 | 1.5 |
| POE(60) hydrogenated castor oil | 1.3 | 1.3 | 1.3 | 1.3 |
| Carboxyvinyl polymer | 0.2 | 0.3 | 0.2 | 0.3 |
| Caustic potash | 0.06 | 0.08 | 0.06 | 0.08 |
| Glycerol | 10 | 10 | 10 | 10 |
| Propylene glycol | 3 | 3 | 3 | 3 |
| Ethyl paraben | 0.2 | 0.2 | 0.2 | 0.2 |
| Purified water | To total amount 100 | | | |
| Vitamin A quantitative determination value | | | | |
| Immediately after preparation (%) | 100 | 100 | 100 | 100 |
| After one month at 40° C. (%) | 97 | 99 | 29 | 22 |

In Examples 6-3 and 6-4, the stability of vitamin A is improved as compared with the Comparative Example. This is the effect according to the present invention.

Quantitative determination method of vitamin A

According to the absorbance determination method at 325 nm using ethanol, the quantitative determination was effected. A sample was prepared by removing vitamin A from Examples and Comparative Examples (control) and the absorption at 325 nm was measured, which was used for correcting an absorbance as the absorbance of a base material.

(absorbance of a sample of Example and Comparative Example at 325 nm)–(an absorbance of a countrol)=the absorbance of vitamin A In the calculation, at the maximum absorption 325 nm, E (1%, 1 cm)=1835 was used.

| Example 6-5: Cosmetic lotion | (% by weight) |
|---|---|
| Oleyl alcohol | 0.002 |
| Benzophenone-12 | 0.001 |
| α-tocopherol | 0.001 |
| Vitamin A | 0.0001 |
| POE(50) Oleyl ether | 0.7 |
| Lactic Acid | 0.1 |
| Sodium lactate | 0.9 |
| Ethanol | 8 |
| Glycerol | 2 |
| Methyl paraben | 0.2 |
| Trisodium edetate | 0.01 |
| Purified water | To total amount 100 |

| Example 6-6: Oil essence | (% by weight) |
|---|---|
| Glycerol tri 2-ethylhexanoate | 30 |
| Octyldodecanol | 20 |
| Squalane | 12 |
| BHT | 1 |
| α-tocopherol | 9 |
| Vitamin A | 8 |
| Dipropylene glycol | 12.899 |
| Ethyl alcohol | 5 |
| Benzophenone | 0.1 |
| Disodium edetate | 0.001 |

| Example 6-7: Cream | (% by weight) |
|---|---|
| Squalane | 15 |
| Glycerol tri 2-ethylhexanoate | 8 |
| isopropyl myristate | 7 |
| BHT | 0.05 |
| BHA | 0.01 |
| α-tocopherol | 0.01 |
| Vitamin A | 0.3 |
| Vaseline | 2 |
| Butyl paraben | 0.1 |
| Propyl paraben | 0.1 |
| Glycerol monooleate | 3 |
| Diglyceroldiisostearate | 2 |
| PEG400 dioleate | 1 |
| Glycerol | 10 |
| Dipropylene glycol | 5 |
| Disodium edetate | 0.01 |
| Benzophenone-6 | 0.1 |
| Benzophenone-4 | 0.03 |
| Triethanolamine | 0.04 |
| Purified water | To total amount 100 |

| Example 6-8: Oil essence | (% by weight) |
|---|---|
| Isopropyl myristate | 10 |
| Octyldodecanol | 20 |
| Squalane | 30 |
| BHT | 1 |
| α-tocopherol | 9 |
| Vitamin A | 1 |
| Dibutyl phthalate | 9 |
| Ethyl alcohol | 9.999 |
| Benzophenone-12 | 7 |
| Benzophenone-6 | 3 |
| Sodium edetate | 0.001 |

| Example 6-9: Oil gel | (% by weight) |
|---|---|
| Glycerol tri 2-ethylhexanoate | 60 |
| POE(20) octyldodecyl ether | 16 |
| Vitamin A | 0.1 |
| Benzophenone-12 | 0.1 |
| Glycerol | 16 |
| Benzophenone-5 | 0.05 |
| Trisodium edetate | 0.02 |
| BHA | 0.01 |
| BHT | 0.01 |
| Purified water | To total amount 100 |

The external skin treatment compositions of Examples 6-5 to 6-9 were excellent in the stability of vitamin A in daily use.

As described hereinabove, in the external skin treatment composition of the present invention, by formulating (A) one or two or more of oil-soluble antioxidant selected from the group consisting of a butyl hydroxytoluene, butyl hydroxyanisole, α,β,γ,δ-tocopherol, nordihydrogualaretin, propyl gallate, a fatty acid ester of vitamin C and sorbic acid, (B) one or two or more of ethylenediaminetetraacetate and (C) one or two or more of benzophenone compound, the stability of vitamin A can be extremely improved.

Production method and temperature test method of Examples 7-1, 7-2 and Comparative Examples 7-1, 7-2

BHT, tocopherol, benzophenone and octylmethoxycinnamate are each completely dissolved in oil at 60° C., then to the resulting solution, is added a solution of sorbic acid and dipropylene glycol dissolved in ethyl alcohol, followed by cooling the resulting solution to 40° C. Thereafter, vitamin A is completely dissolved therein, and the solution is sealed in a brown glass sample tube. The tube is further wrapped with aluminum foil to completely cut light and is stored in a constant temperature bath at 40° C.

TABLE 7-1

Cosmetic oil formulation and vitamin A quantitative determination results (% by weight)

| | Example 7-1 | Example 7-2 | Comp. Example 7-1 | Comp. Example 7-2 |
|---|---|---|---|---|
| Vitamin A | 0.01 | 0.2 | 0.01 | 0.2 |
| BHT | 0.005 | 0.03 | 0.005 | 0.03 |
| dl-α-tocopherol | — | 0.01 | — | 0.01 |
| Benzophenone-3 | 0.05 | 0.1 | — | — |
| Octylmethoxycinnamate | — | — | 0.05 | 0.1 |
| Sorbic acid | 0.001 | 0.005 | — | 0.005 |
| Glycerol tri 2-ethylhexanoate | 45 | 20 | 45 | 20 |
| Isopropyl myristate | 10 | 35 | 10 | 35 |
| Squalane | | To total amount 100 | | |
| Dipropylene glycol | 10 | 10 | 10 | 10 |
| Ethanol | 8 | 8 | 8 | 8 |
| POE(10) Oleyl ether | 2 | 2 | 2 | 2 |
| Vitamin A quantitative determination value | | | | |
| Immediately after preparation (%) | 100 | 100 | 100 | 100 |
| After two months at 40° C. (%) | 95 | 96 | 71 | 69 |

Quantitative determination method of vitamin A

Japanese Pharmacopoeia (11th revision) In accordance with the second method of vitamin A quantitative determinaiton method, the quantitative determinaiton was effected by an absorbance determination method using isopropanol.

In examples 7-1 and 7-2, the stability of vitamin A is improved as compared with the Comparative Example. This is the effect according to the present invention.

Production method and temperature test method of Examples 7-3, 7-4 and Comparative Examples 7-3, 7-4

BHT, tocopherol and benzophenone-2 are each completely dissolved in oil and a surfactant at 70° C., thereafter, immediately before emulsification, vitamin A is completely dissolved therein to form an oil phase.

Glycerol, propylene glycol, carboxyvinyl polymer, caustic potash, ascorbic acid and benzophenone-5 are completely dissolved in purified water. The oil phase is added to the resulting aqueous phase heated to 70° C., then the mixture obtained is emulsified by a homomixer type emulsifier. Then the resulting product is subjected to a cooling treatment by a heat exchanger to 30° C. to form an emulsion.

The emulsion is filled in a glass bottle having a metal coat applied thereto, tightly sealed and is stored in a constant temperature bath at 40° C.

TABLE 7-2

Emulsion formulation and vitamin A quantitative determination results (% by weight)

|  | Example 7-3 | Example 7-4 | Comp. Example 7-3 | Comp. Example 7-4 |
|---|---|---|---|---|
| Vitamin A | 0.3 | 0.01 | 0.3 | 0.01 |
| BHT | 0.05 | 0.01 | 0.05 | 0.01 |
| dl-α-tocopherol | 0.01 | 0.02 | 0.01 | 0.02 |
| Ascorbic acid | 0.05 | 0.05 | 0.05 | — |
| Benzophenone-2 | 0.1 | 0.05 | — | 0.05 |
| Benzophenone-5 | — | 0.05 | — | — |
| Cetyl isooctanoate | 10 | 7 | 10 | 7 |
| Squalane | 5 | 5 | 5 | 5 |
| Cetyl alcohol | 2 | 2 | 2 | 2 |
| Vaseline | 1 | 1 | 1 | 1 |
| Glyceryl-monostearate | 1.5 | 1.5 | 1.5 | 1.5 |
| POE(60) hydrogenated castor oil | 1.3 | 1.3 | 1.3 | 1.3 |
| Carboxyvinyl polymer | 0.2 | 0.3 | 0.2 | 0.3 |
| Caustic potash | 0.06 | 0.08 | 0.06 | 0.08 |
| Glycerol | 10 | 10 | 10 | 10 |
| Propylene glycol | 3 | 3 | 3 | 3 |
| Ethyl paraben | 0.2 | 0.2 | 0.2 | 0.2 |
| Purified water | To total amount 100 | | | |
| Vitamin A quantitative determination value | | | | |
| Immediately after preparation (%) | 100 | 100 | 100 | 100 |
| After two weeks at 40° C. (%) | 96 | 98 | 47 | 41 |

In Examples 7-3 and 7-4, the stability of vitamin A is improved as compared with the Comparative Example. This is the effect according to the present invention.

Quantitative determination method of vitamin A

According to the absorbance determination method at 325 nm using ethanol, the quantitative determination was effected. A sample was prepared by removing vitamin A from Examples and Comparative Examples (control) and the absorption at 325 nm was measured, which was used for correcting an absorbance as the absorbance of a base material.

(absorbance of a sample of Example and Comparative Example at 325 nm)−(absorbance of a control)=the absorbance of vitamin A In the calculation, at the maximum absorption 325 nm, E (1%, 1 cm)=1835 was used.

| Example 7-5: Cosmetic lotion | (% by weight) |
|---|---|
| Oleyl alcohol | 0.002 |
| Benzophenone | 0.001 |
| α-tocopherol | 0.001 |
| Vitamin A | 0.0001 |
| POE(50) Oleyl ether | 0.7 |
| Lactic acid | 0.1 |
| Sodium lactate | 0.9 |
| Ethanol | 8 |
| Glycerol | 2 |
| Methyl paraben | 0.2 |
| Sodium erythorbate (Sodium isoascorbate) | 0.5 |
| Purified water | To total amount 100 |

| Example 7-6: Oil essence | (% by weight) |
|---|---|
| Glycerol tri 2-ethylhexanoate | 10 |
| Octyldodecanol | 20 |
| Squalane | 39 |
| BHT | 1 |
| α-tocopherol | 9 |
| Vitamin A | 1 |
| Dipropylene glycol | 12.89 |
| Ethyl alcohol | 5 |
| Benzophenone | 0.1 |
| Sorbic acid | 0.01 |

| Example 7-7: Cream | (% by weight) |
|---|---|
| Squalane | 15 |
| Glycerol tri 2-ethylhexanoate | 8 |
| Isopropyl myristate | 7 |
| BHT | 0.05 |
| BHA | 0.01 |
| α-tocopherol | 0.01 |
| Vitamin A | 0.3 |
| Vaseline | 2 |
| Butyl paraben | 0.1 |
| Propyl paraben | 0.1 |
| Glycerol monooleate | 3 |
| Diglyceroldiisostearate | 2 |
| PEG400 dioleate | 1 |
| Glycerol | 10 |
| Dipropyl glycol | 5 |
| Sodium ascorbate | 0.01 |
| Benzophenone-8 | 0.1 |
| Benzophenone-4 | 0.03 |
| Triethanolamine | 0.04 |
| Purified water | To total amount 100 |

| Example 7-8: Beauty essence | (% by weight) |
|---|---|
| Glycerol | 30 |
| Propylene glycol | 10 |
| Olive oil | 2 |
| BHT | 0.1 |
| α-tocopherol | 0.1 |
| Vitamin A | 0.1 |
| Ethyl alcohol | 4 |
| Ascorbic acid | 10 |
| Potassium sorbate | 0.1 |
| Gumxanthane | 0.8 |

-continued

| Example 7-8: Beauty essence | (% by weight) |
|---|---|
| POE(60) hydrogenated caster oil | 0.6 |
| Purified water | To total amount 100 |

| Example 7-9: Oil gel | (% by weight) |
|---|---|
| Glycerol tri 2-ethylhexanoate | 60 |
| POE(20) octyldodecyl ether | 16 |
| Vitamin A | 0.1 |
| Benzophenone-12 | 0.1 |
| Glycerol | 16 |
| Erysorbic acid (Isoascorbic acid) | 0.05 |
| Benzophenone-5 | 0.05 |
| BHA | 0.01 |
| BHT | 0.01 |
| Purified water | To total amount 100 |

The external skin treatment compositions of Examples 7-5 to 7-9 were excellent in the stability of vitamin A in daily use.

In the external skin treatment composition of the present invention, by formulating (A) at least one oil-soluble antioxidant selected from the group consisting of a butyl hydroxytoluene, butyl hydroxyanisole, α,β,γ,δ-tocopoherol, nordihydrogualaretin, propyl gallate and a fatty acid ester of vitamin C, (B) at least one compound selected from the group consisting of ascorbic acid, ascorbic acid salt, isoascorbic acid, isoascorbic acid salt, sorbic acid and sorbic acid salt, and (C) at least one benzophenone compound, the stability of vitamin A can be extremely improved.

Examples 8-1 to 8-2 and Comparative Examples 8-1 to 8-2

TABLE 8-1

Vitamin A stability determination results in emulsion (% by weight)

| | Example 8-1 | Example 8-2 | Comp. Example 8-1 | Comp. Example 8-2 |
|---|---|---|---|---|
| Purified water | | To total amount 100 | | |
| Glycerol | 10 | 10 | 10 | 10 |
| Carboxyvinyl polymer | 0.2 | 0.2 | 0.2 | 0.2 |
| Caustic potash | 0.06 | 0.06 | 0.06 | 0.06 |
| Ethyl alcohol | 5 | 5 | 5 | 5 |
| Methyl paraben | 0.1 | 0.1 | 0.1 | 0.1 |
| Cetyl alcohol | 2 | 2 | 2 | 2 |
| Vaseline | 3 | 3 | 3 | 3 |
| Squalane | 5 | 5 | 5 | 5 |
| Isopropyl myristate | 4 | 4 | 4 | 4 |
| Glycerylmonostearate | 1.5 | 1.5 | 1.5 | 1.5 |
| POE(60) hydrogenated castor oil | 2 | 2 | 2 | 2 |
| HP-β-CD | 5 | 5 | — | — |
| BHT | 0.05 | — | 0.05 | — |
| Octylmethoxycinnamate | — | 0.05 | — | 0.05 |
| Vitamin A | 0.3 | 0.3 | 0.3 | 0.3 |
| Vitamin A quantitative determination value | | | | |
| Immediately after preparation (%) | 100 | 100 | 100 | 100 |
| After two weeks at 40° C. (%) | 98 | 93 | 65 | 55 |

As compared with Examples 8-1, 8-2, and the Comparative Examples, the stability of vitamin A is improved. This is the effect according to the present invention.

Quantitative determination method of vitamin A

According to the absorbance determination method at 325 nm using ethanol, the quantitative determination was effected. A sample was prepared by removing vitamin A from Example 8-2 and Comparative Example 8-2 (control) and the absorption at 325 nm was measured, which was used for correcting an absorbance as the absorbance of a base material.

(Absorbance of a sample of Example and Comparative Example at 325 nm)−(Absorbance of a control)= Absorbance of vitamin A In the calculation, at the maximum absorption 325 nm, E (1%, 1 cm)=1835 was used.

TABLE 8-2

Emulsion formulation and vitamin A quantitative determination results (% by weight)

| | Example 8-3 | Example 8-4 | Comp. Example 8-3 | Comp. Example 8-4 |
|---|---|---|---|---|
| β-M-CD | 1 | 1 | — | — |
| α-CD | 3 | 1 | — | — |
| γ-CD | 2 | 1 | — | — |
| BHT | 0.05 | 0.01 | 0.05 | 0.01 |
| dl-α-tocopherol | 0.01 | 0.02 | 0.01 | 0.02 |
| Vitamin A | 0.3 | 0.01 | 0.3 | 0.01 |
| Cetyl isooctanoate | 10 | 7 | 10 | 7 |
| Squalane | 5 | 2 | 5 | 2 |
| Cetyl alcohol | 2 | 2 | 2 | 2 |
| Vaseline | 1 | 1 | 1 | 1 |
| Glyceryl-monostearate | 1.5 | 1.5 | 1.5 | 1.5 |
| POE(60) hydrogenated castor oil | 1.3 | 1.3 | 1.3 | 1.3 |
| Carboxyvinyl polymer | 0.2 | 0.2 | 0.2 | 0.2 |
| Caustic potash | 0.06 | 0.06 | 0.06 | 0.06 |
| Glycerol | 10 | 10 | 10 | 10 |
| Propylene glycol | 3 | 3 | 3 | 3 |
| Methyl paraben | 0.2 | 0.2 | 0.2 | 0.2 |
| Purified water | | To total amount 100 | | |
| Vitamin A quantitative determination value | | | | |
| Immediately after preparation (%) | 100 | 100 | 100 | 100 |
| After one month at 40° C. (%) | 97 | 94 | 60 | 59 |

In Examples 8-3 and 8-4, the stability of vitamin A is improved as compared with the Comparative Example. This is the effect according to the present invention.

Quantitative determination method of vitamin A

In accordance with the second method of vitamin A quantitative determination method, Japanese Pharmacopoeia (11th revision), the quantitative determination was effected by an absorbance determination method using isopropanol.

| Example 8-5: Cosmetic lotion | (% by weight) |
|---|---|
| Oleyl alcohol | 0.002 |
| β-CD | 0.01 |
| BHA | 0.001 |
| Vitamin A | 0.0001 |
| POE(50) Oleyl ether | 0.7 |
| Lactic acid | 0.01 |

| Example 8-5: Cosmetic lotion | (% by weight) |
|---|---|
| Sodium lactate | 0.09 |
| Ethanol | 5 |
| Glycerol | 1 |
| Methyl paraben | 0.2 |
| Purified water | To total amount 100 |

| Example 8-6: Beauty essence | (% by weight) |
|---|---|
| HP-β-CD | 30 |
| BHT | 1 |
| Vitamin A | 1 |
| Isopropyl myristate | 10 |
| POE(60) hydrogenated caster oil | 1 |
| POE(20) sorbitan laurate | 1 |
| Carboxyvinyl polymer | 0.3 |
| Triethanolamine | 2.3 |
| Ethanol | 3 |
| Methyl paraben | 0.1 |
| Purified water | To total amount 100 |

| Example 8-7: Cream | (% by weight) |
|---|---|
| HE-β-CD | 3 |
| BHT | 0.01 |
| 2-hydroxy-4-methoxybenzophenone | 0.02 |
| Vitamin A | 0.3 |
| Glycerol tri-2-ethylhexanoate | 10 |
| Vaseline | 2 |
| Squalane | 18 |
| Butyl paraben | 0.1 |
| Propyl paraben | 0.1 |
| Glycerol monooleate | 3 |
| Diglyceroldiisostearate | 2 |
| PEG400 dioleate | 1 |
| Glycerol | 10 |
| Dipropylele glycol | 5 |
| Purified water | To total amount 100 |

| Example 8-8: Cosmetic lotion | (% by weight) |
|---|---|
| Vitamin A | 0.001 |
| BHT inclusion-β-HPCD (BHT:β-HPCD = 1:100) | 5 |
| Glycerol | 2 |
| Citric acid | 0.03 |
| Trisodium citrate | 0.07 |
| Ethanol | 5 |
| Methyl paraben | 0.1 |
| Purified water | To total amount 100 |

| Example 8-9: Beauty powder | (% by weight) |
|---|---|
| Vitamin A | 0.3 |
| α-tocopherolinclusion-α-CD (α-tocopherol:α-CD = 1:150) | 10 |
| Ultraviolet absorber inclusion-β-HPCD* (Ultraviolet absorber:β-HPCD = 1:150) | 30 |
| D-mannitol | To total amount 100 |

*: Ultraviolet absorber: Octylmethoxycinnamate

The external skin treatment compositions of Examples 8-5 to 8-9 were excellent in the stability of vitamin A in daily use.

As described hereinabove, in the external skin treatment composition of the present invention, by formulating cyclodextrin including an antioxidant and/or an ultraviolet absorber, the stability of vitamin A can be extremely improved.

Examples 9-1 to 9-2 and Comparative Examples 9-1 to 9-2

TABLE 9-1

Vitamin A stability determination results in emulsion (% by weight)

| | Example 9-1 | Example 9-2 | Comp. Example 9-1 | Comp. Example 9-2 |
|---|---|---|---|---|
| Purified water | To total amount 100 | | | |
| Glycerol | 10 | 10 | 10 | 10 |
| Carboxyvinyl polymer | 0.2 | 0.2 | 0.2 | 0.2 |
| Caustic potash | 0.06 | 0.06 | 0.06 | 0.06 |
| Ethyl alcohol | 5 | 5 | 5 | 5 |
| Methyl paraben | 0.1 | 0.1 | 0.1 | 0.1 |
| Cetyl alcohol | 2 | 2 | 2 | 2 |
| Vaseline | 3 | 3 | 3 | 3 |
| Squalane | 5 | 5 | 5 | 5 |
| Isopropyl myristate | 4 | 4 | 4 | 4 |
| Butylhydroxytoluene | 0.05 | 0.05 | 0.05 | 0.05 |
| Glyceryl monostearate | 1.5 | 1.5 | 1.5 | 1.5 |
| POE(60) hydrogenated castor oil | 2 | 2 | 2 | 2 |
| 1,3-butanediol | 0.01 | 5 | — | — |
| Propylene glycol | — | — | 5 | — |
| Dipropylene glycol | — | — | — | 5 |
| Vitamin A | 0.3 | 0.3 | 0.3 | 0.3 |
| Vitamin A quantitative determination value | | | | |
| Immediately after preparation (%) | 100 | 100 | 100 | 100 |
| After one month at 40° C. (%) | 93 | 92 | 65 | 69 |

In Examples 9-1 and 9-2, the stability of vitamin A is improved as compared with the Comparative Example. This is the effect according to the present invention.

Quantitative determination method of vitamin A

In accordance with the second method of vitamin A quantitative determination method, Japanese Pharmacopoeia (11th revision), the quantitative determination was effected by an absorbance determination method using isopropanol.

| Example 9-3: Cream | | (% by weight) |
|---|---|---|
| A. | Cetanol | 3 |
| | Glycerylmonostearate | 2 |
| | POE(25) Cetyl ether | 1 |
| | Stearic acid | 3 |
| | Vaseline | 3 |
| | Olive oil | 3 |
| | Isopropyl myristate | 1 |
| | Squalane | 5 |
| | Vitamin A | 0.1 |
| | BHT | 0.05 |
| | Perfume | q.s. |
| B. | 1,2-butanediol | 3 |
| | 1,3-butanediol | 3 |

-continued

| Example 9-3: Cream | (% by weight) |
|---|---|
| 1,4-butanediol | 3 |
| Potassium hydroxide | 0.2 |
| Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 9-4: Beauty essence | (% by weight) |
|---|---|
| Carboxyvinyl polymer | 0.3 |
| 1,3-butanediol | 25 |
| 1,4-butanediol | 15 |
| Glycerol | 30 |
| Triethanolamine | 3.5 |
| POE(60) hydrogenated castor oil | 0.5 |
| Vitamin A | 0.1 |
| Squalane | 1 |
| α-tocopherol | 0.01 |
| Methyl paraben | 0.2 |
| Ethyl alcohol | 6 |
| Purified water | To total amount 100 |

| Example 9-5: Cosmetic lotion | (% by weight) |
|---|---|
| 1,3-butanediol | 5 |
| Ethanol | 7 |
| POE(50) Oleyl ether | 0.5 |
| Oleyl alcohol | 0.002 |
| Vitamin A | 0.0001 |
| BHT | 0.001 |
| Citric acid | 0.03 |
| Trisodium citrate | 0.07 |
| Methyl paraben | 0.1 |
| Disodium edetate | 0.03 |
| Purified water | To total amount 100 |

| Example 9-6: Oil essence | (% by weight) |
|---|---|
| Vitamin A | 1 |
| Glycerol tri 2-ethylhexanoate | 69 |
| Olive oil | 10 |
| BHT | 1 |
| α-tocopherol | 9 |
| 1,3-butanediol | 5 |
| Squalane | 5 |

| Example 9-7: Night cream | (% by weight) |
|---|---|
| Vaseline | 4 |
| Squalane | 15 |
| Liquid paraffin | 5 |
| Cetyl octanoate | 5 |
| Glycerylmonooleate | 4 |
| POE(5) hydrogenated castor oil | 1 |
| Butyl paraben | 0.2 |
| Vitamin A | 0.2 |
| 1,4-butanediol | 2 |
| 1,3-butanediol | 8 |

-continued

| Example 9-7: Night cream | (% by weight) |
|---|---|
| Glycerol | 12 |
| Trisodium edetate | 0.03 |
| Purified water | To total amount 100 |

The external skin treatment compositions of Examples 9-3 to 9-7 were excellent in the stability of vitamin A in daily use. As described hereinabove, in the external skin treatment composition of the present invention, by formulating butanediol and an oil-soluble antioxidant, stability of vitamin A can be extremely improved.

Examples 10-1, 10-2 and Comparative Examples 10-1, 10-2

Tocopherol, octylmethoxycinnamate, oleyl alcohol, methyl paraben, POE(20) octyldodecyl ether are completely dissolved in ethanol at 40° C., thereafter, vitamin A is completely dissolved therein, and the solution is quickly cooled to form an alcohol portion. The resulting alcohol portion is added to an aqueous portion wherein other components are dissolved in purified water, and sealed in a brown glass sample tube. The tube is further wrapped with aluminum foil to completely cut light and is stored in a constant temperature bath at 40° C.

TABLE 10-1

Vitamin A stability determination results in lotion (% by weight)

| | Example 10-1 | Example 10-2 | Comp. Example 10-1 | Comp. Example 10-2 |
|---|---|---|---|---|
| Vitamin A | 0.001 | 0.001 | 0.001 | 0.001 |
| Oleyl alcohol | 0.005 | 0.005 | 0.005 | 0.005 |
| Octylmethoxycinnamate | — | — | 0.001 | — |
| Benzophenone-5 | 0.001 | 0.1 | — | — |
| Benzophenone-3 | — | — | — | 0.01 |
| POE(20) Octyldodecyl ether | 0.8 | 0.8 | 0.8 | 0.8 |
| Ethanol | 18 | 18 | 18 | 18 |
| Glycerol | 3 | 3 | 3 | 3 |
| Methyl paraben | 0.1 | 0.1 | 0.1 | 0.1 |
| Citric acid | 0.03 | 0.03 | 0.03 | 0.03 |
| Trisodium citrate | 0.07 | 0.07 | 0.07 | 0.07 |
| Trisodium edetate | 0.02 | 0.02 | 0.02 | 0.02 |
| Purified water | To total amount 100 | | | |
| Vitamin A quantitative determination value | | | | |
| Immediately after preparation (%) | 100 | 100 | 100 | 100 |
| After one month at 40° C. (%) | 92 | 95 | 49 | 52 |

Quantitative determination method of vitamin A

In accordance with the second method of vitamin A quantitative determination method, Japanese Pharmacopoeia (11th revision), the quantitative determination was effected by an absorbance determination method using isopropanol.

In Examples 10-1 and 10-2, the stability of vitamin A is improved as compared with the Comparative Example. This is the effect produced by the addition of a water-soluble benzophenone compound according to the present invention.

Examples 10-3 to 10-4 and Comparative Examples 10-3 to 10-4

TABLE 10-2

Emulsion formulation and vitamin A quantitative determination results (% by weight)

|  | Example 10-3 | Example 10-4 | Comp. Example 10-3 | Comp. Example 10-3 |
|---|---|---|---|---|
| Vitamin A | 0.3 | 0.01 | 0.3 | 0.01 |
| BHT | 0.05 | 0.01 | 0.05 | 0.01 |
| dl-α-tocopherol | 0.01 | 0.02 | 0.01 | 0.02 |
| Benzophenone-5 | 0.1 | 0.05 | — | — |
| Benzophenone-9 | — | 0.05 | — | — |
| Octylmethoxycinnamate | — | — | 0.1 | — |
| Methoxybenzoylmethane* | — | — | — | 0.1 |
| Cetyl isooctanoate | 10 | 7 | 10 | 7 |
| Squalane | 5 | 5 | 5 | 5 |
| Cetyl alcohol | 2 | 2 | 2 | 2 |
| Vaseline | 1 | 1 | 1 | 1 |
| Glyceryl monostearate | 1.5 | 1.5 | 1.5 | 1.5 |
| POE(60) hydrogenated castor oil | 1.3 | 1.3 | 1.3 | 1.3 |
| Carboxyvinyl polymer | 0.2 | 0.3 | 0.2 | 0.3 |
| Caustic potash | 0.06 | 0.08 | 0.06 | 0.08 |
| Glycerol | 10 | 10 | 10 | 10 |
| Propylene glycol | 3 | 3 | 3 | 3 |
| Ethyl paraben | 0.2 | 0.2 | 0.2 | 0.2 |
| Purified water | To total amount 100 | | | |
| Vitamin A quantitative determination value | | | | |
| Immediately after preparation (%) | 100 | 100 | 100 | 100 |
| After one month at 40° C. (%) | 97 | 99 | 29 | 22 |

*4-(1,1-dimethylethyl)-4'-methoxybenzoylmethane

Each oil component containing BHT, and tocopherol, and a surfactant are completely dissolved at 70° C., thereafter, immediately before emulsification, vitamin A is completely dissolved therein to form an oil phase.

Glycerol, propylene glycol, carboxyvinyl polymer, caustic potash, benzophenone-9 and benzophenone-5 are completely dissolved in purified water. The oil phase is added to the resulting aqueous phase heated to 70° C., then the mixture obtained is emulsified by a homomixer type emulsifier. Then, the resulting product is subjected to a cooling treatment by a heat exchanger to 30° C. to form an emulsion.

The emulsion is filled in a glass bottle having a metal coat applied thereto, which is tightly sealed and is stored in a constant temperature bath at 40° C.

In Examples 10-3 to 10-4, as compared with the Comparative Example, the stability of vitamin A is improved. This is the effect according to the present invention.

Quantitative determination method of vitamin A

According to the absorbance determination method at 325 nm using ethanol, the quantitative determination was effected. A sample was prepared by removing vitamin A from Example and Comparative Example (control) and the absorption at 325 nm was measured, which was used for correcting an absorbance as the absorbance of a base material.

(Absorbance of a sample of Example and Comparative Example at 325 nm)−(Absorbance of a control)= Absorbance of vitamin A In the calculation, at the maximum absorption 325 nm, E (1%, 1 cm)=1835 was used.

| Example 10-5: Cosmetic lotion | (% by weight) |
|---|---|
| Oleyl alcohol | 0.002 |
| Vitamin A | 0.0001 |
| POE(50) Oleyl ether | 0.7 |
| Lactic acid | 0.01 |
| Trisodium citrate | 0.09 |
| Ethanol | 8 |
| Glycerol | 2 |
| Methyl paraben | 0.2 |
| Benzophenone-12 | 2.5 |
| Benzophenone-5 | 2.5 |
| Purified water | To total amount 100 |

| Example 10-6: Oil essence | (% by weight) |
|---|---|
| Glycerol tri 2-ethylhexanoate | 34 |
| Isopropyl myristate | 35 |
| Dibutyl phthalate | 10 |
| Vitamin A | 1 |
| Diglyceroldiisostearate | 5 |
| Dipropylene glycol | 14.997 |
| Benzophenone-4 | 0.001 |
| Trisodium citrate | 0.002 |

| Example 10-7: Cream | (% by weight) |
|---|---|
| Squalane | 15 |
| Glycerol tri 2-ethylhexanoate | 8 |
| Isopropyl myristate | 7 |
| α-tocopherol | 0.05 |
| Vitamin A | 0.3 |
| Vaseline | 2 |
| Butyl paraben | 0.1 |
| Propyl paraben | 0.1 |
| Glycerol monooleate | 3 |
| Diglyceroldiisostearate | 2 |
| PEG400 dioleate | 1 |
| Glycerol | 10 |
| Dipropylene glycol | 5 |
| Disodium edetate | 0.01 |
| Benzophenone-4 | 0.03 |
| Triethanolamine | 0.04 |
| Purified water | To total amount 100 |

| Example 10-8: Oil gel | (% by weight) |
|---|---|
| Glycerol tri 2-ethylhexanoate | 60 |
| POE(20) octyldodecyl ether | 16 |
| Vitamin A | 0.1 |
| Glycerol | 16 |
| Benzophenone-5 | 0.05 |
| Purified water | To total amount 100 |

The external skin treatment compositions of Examples 10-5 to 10-8 were excellent in the stability of vitamin A in daily use. As described hereinabove, in the external skin treatment composition of the present invention, by formulating a water-soluble benzophenone compound, stability of vitamin A can be extremely improved.

Examples 11-1 to 11-3 and Comparative Example 11-1

TABLE 11-1

Vitamin A stability determination results in emulsion (% by weight)

|  | Example 11-1 | Example 11-2 | Example 11-3 | Comp. Example 11-1 |
|---|---|---|---|---|
| Purified water | | To total amount 100 | | |
| Glycerol | 10 | 10 | 10 | 10 |
| Carboxyvinyl polymer | 0.2 | 0.2 | 0.2 | 0.2 |
| Arginine | 0.21 | 0.28 | 0.42 | 0.06 |
| Caustic potash | — | — | — | 0.06 |
| Ethyl alcohol | 5 | 5 | 5 | 5 |
| Methyl paraben | 0.1 | 0.1 | 0.1 | 0.1 |
| Cetyl alcohol | 2 | 2 | 2 | 2 |
| Vaseline | 3 | 3 | 3 | 3 |
| Squalane | 5 | 5 | 5 | 5 |
| Isopropyl myristate | 4 | 4 | 4 | 4 |
| Glycerylmonostearate | 1.5 | 1.5 | 1.5 | 1.5 |
| POE(60) hydrogenated castor oil | 2 | 2 | 2 | 2 |
| Butylhydroxytoluene | 0.05 | 0.05 | 0.05 | 0.05 |
| Vitamin A | 0.3 | 0.3 | 0.3 | 0.3 |
| pH (25° C.) | 5.7 | 6.6 | 7.4 | 5.8 |
| Vitamin quantitative determination value | | | | |
| Immediately after preparation (%) | 100 | 100 | 100 | 100 |
| After one month at 40° C. (%) | 90 | 92 | 95 | 71 |

In Examples 11-1, 11-2, and 11-3, the stability of vitamin A is improved as compared with the Comparative Example. This is the effect according to the present invention.

Quantitative determination method of vitamin A

In accordance with the second method of vitamin A quantitative determination method, Japanese Pharmacopoeia (11th revision), the quantitative determination was effected by an absorbance determination method using isopropanol.

| Example 11-4: Cream | | (% by weight) |
|---|---|---|
| A. | Cetanol | 3 |
| | Glycerylmonostearate | 2 |
| | POE(25) Cetyl ether | 2 |
| | Stearic acid | 3 |
| | Vaseline | 2 |
| | Olive oil | 3 |
| | Isopropyl myristate | 3 |
| | Squalane | 5 |
| | Vitamin A | 0.1 |
| | BHT | 0.05 |
| | Perfume | q.s. |
| B. | Propylene glycol | 3 |
| | Potassium hydroxide | 0.27 |
| | Arginine | 0.001 |
| | Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream. (pH=7.3)

| Example 11-5: Beauty essence | (% by weight) |
|---|---|
| Carboxyvinyl polymer | 0.4 |
| Glycerol | 5 |
| Propyl glycol | 5 |
| Lysine | 0.5 |
| Arginine | 4.8 |
| POE(60) hydrogenated castor oil | 0.5 |
| Vitamin A | 0.1 |
| Squalane | 1 |
| α-tocopherol | 0.05 |
| Methyl paraben | 0.2 |
| Ethyl alcohol | 6 |
| Purified water | To total amount 100 |
| | pH = 6.7 |

| Example 11-6: Cosmetic lotion | (% by weight) |
|---|---|
| Glycerol | 2 |
| Ethanol | 7 |
| POE(50) Oleyl ether | 0.5 |
| Oleyl alcohol | 0.002 |
| Vitamin A | 0.0001 |
| Lactic acid | 0.03 |
| Arginine | 0.1 |
| Ornithine hydrochloride | 1 |
| Methyl paraben | 0.1 |
| Purified water | To total amount 100 |
| | pH = 6.2 |

| Example 11-7: Oil gel | (% by weight) |
|---|---|
| Vitamin A | 0.5 |
| Glycerol tri 2-ethylhexanoate | 40 |
| Olive oil | 10 |
| BHT | 0.1 |
| BHA | 0.05 |
| PHE(20) octyldodecyl ether | 16 |
| Glycerol | 15 |
| Lysine hydrochloride | 0.1 |
| Purified water | To total amount 100 |
| | pH = 5.5 |

| Example 11-8: Night cream | (% by weight) |
|---|---|
| Solid paraffin | 1 |
| Microcrystalline wax | 2 |
| Beeswax | 1 |
| Squalane | 15 |
| Glycerol tri 2-ethylhexanoate | 10 |
| Diglycerol diisostearate | 3 |
| PEG400 diisostearate | 1 |
| Propyl paraben | 0.2 |
| Vitamin A | 0.3 |
| Glycerol | 10 |
| Propylene glycol | 4 |
| Arginine | 0.2 |
| Pyrrolidone carboxylic acid | 0.2 |
| Purified water | To total amount 100 |

The external skin treatment compositions of Examples 11-4 to 11-8 were excellent in the stability of vitamin A in daily use.

In the external skin treatment composition of the present invention, by formulating a basic amino acid and/or the salt thereof, stability of vitamin A can be extremely improved.

Examples 12-1 to 12-3 and Comparative Example 12-1

TABLE 12-1

Vitamin A stability determination results in emulsion (% by weight)

|  | Example 12-1 | Example 12-2 | Example 12-3 | Comp. Example 12-1 |
|---|---|---|---|---|
| Purified water | | To total amount 100 | | |
| Glycerol | 10 | 10 | 10 | 10 |
| Carboxyvinyl polymer | 0.2 | 0.2 | 0.2 | 0.2 |
| Caustic potash | 0.06 | 0.06 | 0.06 | 0.06 |
| Ethyl alcohol | 5 | 5 | 5 | 5 |
| Methyl paraben | 0.1 | 0.1 | 0.1 | 0.1 |
| Cetyl alcohol | 2 | 2 | 2 | 2 |
| Butyl alcohol | 1 | 1 | 1 | 1 |
| Vaseline | 3 | 3 | 3 | 3 |
| Squalane | 5 | 5 | 5 | 5 |
| Isopropyl myristate | 4 | 4 | 4 | 4 |
| Glycerylmonostearate | 1.5 | 1.5 | 1.5 | 1.5 |
| POE(60) hydrogenated castor oil | 2 | 2 | 2 | 2 |
| BHT | 0.03 | 0.03 | 0.03 | 0.03 |
| Trisodium edetate | 0.02 | 0.02 | 0.02 | 0.02 |
| Arginine aspartate | 0.03 | 0.03 | — | — |
| Monosodium glutamate | — | 0.5 | 0.01 | — |
| Vitamin A | 0.3 | 0.3 | 0.3 | 0.3 |
| Vitamin A quantitative determination value | | | | |
| Immediately after preparation (%) | 100 | 100 | 100 | 100 |
| After two months at 40° C. (%) | 90 | 96 | 90 | 69 |

In Examples 12-1, 12-2 and 12-3, the stability of vitamin A is improved as compared with the Comparative Example. This is the effect according to the present invention.

Quantitative determination method of vitamin A

In accordance with the second method of vitamin A quantitative determination method, Japanese Pharmacopoeia (11th revision), the quantitative determination was effected by an absorbance determination method using isopropanol.

| Example 12-4: Cream | | (% by weight) |
|---|---|---|
| A. | Cetanol | 3 |
| | Glycerylmonostearate | 2 |
| | POE(25) Cetyl ether | 1 |
| | Stearic acid | 3 |
| | Vaseline | 3 |
| | Olive oil | 3 |
| | Isopropyl myristate | 1 |
| | Squalane | 5 |
| | Vitamin A | 0.1 |
| | BHT | 0.05 |
| | Perfume | q.s. |
| B. | Propylene glycol | 3 |
| | Potassium hydroxide | 0.2 |
| | Monosodium glutamate | 5 |
| | Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 12-5: Beauty essence | (% by weight) |
|---|---|
| Carboxyvinyl polymer | 0.4 |
| Glycerol | 5 |
| Propylene glycol | 5 |
| Arginine aspartate | 0.001 |
| Triethanolamine | 3.4 |
| POE(60) hydrogenated castor oil | 0.5 |
| Vitamin A | 0.001 |
| Squalane | 1 |
| α-tocopherol | 1 |
| Methyl paraben | 0.2 |
| Ethyl alcohol | 6 |
| Purified water | To total amount 100 |

| Example 12-6: Cosmetic lotion | (% by weight) |
|---|---|
| Glycerol | 2 |
| Ethanol | 7 |
| POE(50) Oleyl ether | 0.5 |
| Oleyl alcohol | 0.002 |
| Vitamin A | 0.0001 |
| Aspartic acid | 0.001 |
| Lactic acid | 0.02 |
| Sodium lactate | 0.1 |
| Methyl paraben | 0.1 |
| Purified water | To total amount 100 |

| Example 12-7: Oil gel | (% by weight) |
|---|---|
| Vitamin A | 1 |
| Glycerol tri 2-ethylhexanoate | 40 |
| Oliver oil | 19 |
| BHT | 0.1 |
| BHA | 0.05 |
| POE(20) octyldodecyl ether | 16 |
| Glycerol | 15 |
| Sodium glutamate | 0.01 |
| Purified water | To total amount 100 |

| Example 12-8: Beauty liquid | (% by weight) |
|---|---|
| Vitamin A | 0.3 |
| Isopropyl myristate | 3 |
| POE(60) hydrogenated castor oil | 0.6 |
| Gum xanthane | 0.8 |
| Glycerol | 30 |
| Propylene glycol | 5 |
| Sodium pyrrolidone carboxylate (50%) | 20 |
| Ethanol | 6 |
| Methyl paraben | 0.1 |
| Purified water | To total amount 100 |

| Example 12-9: Night cream | (% by weight) |
|---|---|
| Squalane | 15 |
| Microcrystalline wax | 4 |
| Isopropyl myristate | 5 |
| Vaseline | 4 |
| Octyl dodecanol | 2 |
| Butyl paraben | 0.15 |
| Vitamin A | 0.2 |

-continued

| Example 12-9: Night cream | (% by weight) |
|---|---|
| Diglycerol diisostearate | 4 |
| Glycerol | 3 |
| Propylene glycol | 3 |
| Sodium glutamate | 1 |
| Purified water | To total amount 100 |

The external skin treatment compositions of Examples 12-4 to 12-9 were excellent in the stability of vitamin A in daily use.

In the external skin treatment composition of the present invention, by formulating an acidic amino acid and/or the salt thereof, stability of vitamin A can be extremely improved.

Examples 13-1 to 13-3 and Comparative Examples 13-1 to 13-2

TABLE 13-1

Vitamin A stability determination results in oil (% by weight)

| | Example 13-1 | Example 13-2 | Example 13-3 | Comp. Example 13-1 | Comp. Example 13-2 |
|---|---|---|---|---|---|
| Vitamin A | 1 | 1 | 1 | 1 | 1 |
| Pentaerythritol ester | 99 | 49 | — | — | — |
| Trimethylolpropane ester | — | 50 | 99 | — | — |
| Squalane | — | — | — | 99 | — |
| Cetylisooctanoate | — | — | — | — | 99 |
| Vitamin A quantitative determination value | | | | | |
| Immediately after preparation (%) | 99 | 100 | 99 | 100 | 100 |
| After one month at 40° C. (%) | 96 | 94 | 92 | 40 | 51 |

Pentaerythritol ester: pentaerythrito-tetra(2-ethylhexanoate) ester
Trimethylolpropane ester: trimethylolpropane-tri(2-ethyl-hexanoate)ester Quantitative determination method of vitamin A In accordance with the second method of vitamin A quantitative determination method, Japanese Pharmacopoeia (11th revision), the quantitative determination was effected by an absorbance determination method using isopropanol.

In Examples 13-1, 13-2, and 13-3, the stability of vitamin A is improved as compared with the Comparative Example. This is the effect according to the present invention.

Examples 13-4, 13-5 and Comparative Examples 13-3, 13-4

BHT and tocopherol are each completely dissolved in oil at 60° C., then the resulting solution is cooled to 40° C. Thereafter, vitamin A is completely dissolved therein. The resulting solution is filled in a brown glass sample tube and is stored in a constant temperature bath at 40° C.

TABLE 13-2

Cosmetic oil formulation and vitamin A stability determination results (% by weight)

| | Example 13-4 | Example 13-5 | Comp. Example 13-3 | Comp. Example 13-4 |
|---|---|---|---|---|
| Trimethylolpropane (2-ethylhexanoate) | 75 | 10 | — | — |
| Pentaerythritol (2-ethylhexanoate) | — | 80 | — | — |
| Dimethylpolysiloxane | — | 9.76 | — | 39.76 |
| Isopropylmyristate | — | — | 15 | 60 |
| Squalane | 24.985 | — | 84.985 | — |
| Vitamin A | 0.01 | 0.2 | 0.01 | 0.2 |
| BHT | 0.005 | 0.03 | 0.005 | 0.03 |
| dl-α-tocopherol | — | 0.01 | — | 0.01 |
| Vitamin A quantitative determination value | | | | |
| Immediately after preparation (%) | 100 | 100 | 100 | 100 |
| After two months at 40° C. (%) | 96 | 97 | 59 | 73 |

In Examples 13-4 and 13-5, as compared with the Comparative Example, the stability of vitamin A is improved. This is the effect according to the present invention.

Production method and temperature test method of Examples 13-6, 13-7 and Comparative Examples 13-5, 13-6

BHT, tocopherol and each oil and a surfactant are completely dissolved at 70° C., thereafter, immediately before emulsification, vitamin A is completely dissolved therein to form an oil phase.

Glycerol, propylene glycol, carboxyvinyl polymer and caustic potash are completely dissolved in purified water. The oil phase is added to the resulting aqueous phase heated to 70° C., then the mixture obtained is emulsified by a homomixer type emulsifier. Then the resulting product is subjected to a cooling treatment by a heat exchanger to 30° C. to form an emulsion.

The emulsion is filled in a glass bottle having a metal coat applied thereto, which is tightly sealed and is stored in a constant temperature bath at 40° C.

TABLE 13-3

Emulsion formulation and vitamin A quantitative determination results (% by weight)

| | Example 13-6 | Example 13-7 | Comp. Example 13-5 | Comp. Example 13-6 |
|---|---|---|---|---|
| Pentaerythritol (2-ethylhexanoate) | 10 | 4 | — | — |
| Trimethylolpropane (2-ethylhexanoate) | — | 3 | — | — |
| BHT | 0.05 | 0.01 | 0.05 | 0.01 |
| dl-α-tocopherol | 0.01 | 0.02 | 0.01 | 0.02 |
| Vitamin A | 0.3 | 0.01 | 0.3 | 0.01 |
| Cetylisooctanoate | — | — | 10 | 7 |
| Squalane | 5 | 2 | 5 | 2 |
| Cetyl alcohol | 2 | 2 | 2 | 2 |
| Vaseline | 1 | 1 | 1 | 1 |
| Glyceryl monostearate POE(60) | 1.5 | 1.5 | 1.5 | 1.5 |
| Hydrogenated castor oil | 1.3 | 1.3 | 1.3 | 1.3 |
| Carboxyvinyl polymer | 0.2 | 0.2 | 0.2 | 0.2 |
| Caustic Potash | 0.06 | 0.06 | 0.06 | 0.06 |
| Glycerol | 10 | 10 | 10 | 10 |

TABLE 13-3-continued

Emulsion formulation and vitamin A quantitative determination results (% by weight)

|  | Example 13-6 | Example 13-7 | Comp. Example 13-5 | Comp. Example 13-6 |
|---|---|---|---|---|
| Propylene glycol | 3 | 3 | 3 | 3 |
| Ethyl paraben | 0.2 | 0.2 | 0.2 | 0.2 |
| Purified water | To total amount 100 | | | |
| Vitamin A quantitative determination value | | | | |
| Immediately after preparation (%) | 100 | 100 | 100 | 100 |
| After one month at 40° C. (%) | 98 | 96 | 32 | 25 |

In Examples 13-6 and 13-7, the stability of vitamin A is improved as compared with the Comparative Example. This is the effect according to the present invention.

Quantitative determination method of vitamin A

According to the absorbance determination method at 325 nm using ethanol, the quantitative determination was effected.

In the calculation, at the maximum absorption 325 nm, E (1%, 1 cm)=1835 was used

| Example 13-8: Cosmetic lotion | (% by weight) |
|---|---|
| Pentaerythritoltetracaprate | 0.002 |
| -tocopherol | 0.001 |
| α-tocopherol | 0.0005 |
| Vitamin A | 0.0001 |
| POE(50) Oleylether | 0.7 |
| Lactic acid | 0.1 |
| Sodium lactate | 0.9 |
| Ethanol | 5 |
| Glycerol | 1 |
| Methyl paraben | 0.2 |
| Trisodium edetate | 0.01 |
| Purified water | To total amount 100 |

| Example 13-9: Oil essence | (% by weight) |
|---|---|
| Pentaerythritoltetra (2-hexanoate) | 60 |
| Trimethyrolpropanetricaprate | 10 |
| Squalane | 10 |
| BHT | 1 |
| α-tocopherol | 9 |
| Vitamin A | 5 |

| Example 13-10: Cream | (% by weight) |
|---|---|
| Glycerol tri 2-ethylhexanoate | 10 |
| Pentaerythritoltetra (2-ethylhexanoate) | 15 |
| BHT | 0.05 |
| BHA | 0.01 |
| α-tocopherol | 0.01 |
| Vitamin A | 0.3 |
| Vaseline | 2 |
| Squalane | 8 |
| Butyl paraben | 0.1 |
| Propyl paraben | 0.1 |
| Glycerol monooleate | 3 |
| Diglycerol diisostearate | 2 |

-continued

| Example 13-10: Cream | (% by weight) |
|---|---|
| PEG400 dioleate | 1 |
| Glycerol | 10 |
| Dipropylene glycol | 5 |
| Purified water | Tototalamount100 |

| Example 13-11: Eye wrinkle oil | (% by weight) |
|---|---|
| Pentaerythritoitetra(2-ethylhexanoate) | 40 |
| Trimethyrolpropanetricaprate | 20 |
| Glycerol tri 2-ethylhexanoate | 20 |
| Squalane | 19 |
| Acetic acid palmitate | 1 |

The external skin treatment compositions of Examples 13-8 to 13-11 were excellent in the stability of vitamin A in daily use.

In the external skin treatment composition of the present invention, by formulating at least one polar oil component selected from the group cosisting of pentaerythritol fatty acid ester and trimethylol propane fatty acid ester, the stability of vitamin A can be improved.

In accordance with the present invention, by formulating at least one polar oil selected from the group consisting of pentaerythritol fatty acid ester and trimethylolpropane fatty acid ester, and at least one oil-soluble antioxidant selected from the group consisting of butyl hydroxytoluene, butyl hydroxyanisole, α,β,γ,δ-tocopherol, nordihydrogualaretin, propyl gallate, a fatty acid ester of vitamin C and sorbic acid, the stability of vitamin A can be further noticeably improved.

Examples 14-1 to 14-2 and Comparative Examples 14-1 to 14-2

TABLE 14-1

Vitamin A stability determination results in emulsion (% by weight)

|  | Example 14-1 | Example 14-2 | Comp. Example 14-1 | Comp. Example 14-2 |
|---|---|---|---|---|
| Purified water | To total amount 100 | | | |
| Glycerol | 10 | 10 | 10 | 10 |
| Ethyl alcohol | 5 | 5 | 5 | 5 |
| Methyl paraben | 0.1 | 0.1 | 0.1 | 0.1 |
| Glyceryl monostearate | 1.5 | 1.5 | 1.5 | 1.5 |
| POE(60) hydrogenated castor oil | 2 | 2 | 2 | 2 |
| Cetyl alcohol | 2 | 2 | 2 | 2 |
| Isopropyl myristate | 4 | 4 | 4 | 4 |
| Vaseline | 3 | 3 | 3 | 3 |
| Squalane | 5 | 5 | 5 | 5 |
| BHT | — | 0.05 | — | 0.05 |
| Trisodium edetate | — | 0.03 | — | 0.03 |
| Natural montmorillonite | 2 | 2 | — | — |
| Vitamin A | 0.3 | 0.3 | 0.3 | 0.3 |
| Vitamin A quantitative determination value | | | | |
| Immediately after preparation (%) | 100 | 100 | 100 | 100 |
| After one month at 40° C. (%) | 90 | 95 | 53 | 68 |

*Natural montmorillonite: Trade name Kunipia G-4

Quantitative determination method of vitanin A

In accordance with the second method of vitamin A quantitative determination method, Japanese Pharmacopoeia (11th revision), the quantitative determination was effected by an absorbance determination method using isopropanol.

In Examples 14-1, 14-2, the stability of vitamin A is improved as compared with Comparative Example. This is the effect according to the present invention.

TABLE 14-2

Emulsion formulation and vitamin A quantitative determination results (% by weight)

|  | Example 14-3 | Example 14-4 | Comp. Example 14-3 | Comp. Example 14-4 |
|---|---|---|---|---|
| Natural saponite (Veegum HV) | 3 | 3 | — | — |
| Ascorbic acid | 0.1 | — | 0.1 | — |
| BHT | 0.05 | 0.01 | 0.05 | 0.01 |
| dl-α-tocopherol | 0.01 | 0.02 | 0.01 | 0.02 |
| Vitamin A | 0.3 | 0.01 | 0.3 | 0.01 |
| Cetylisooctanoate | 10 | 7 | 10 | 7 |
| Squalane | 5 | 2 | 5 | 2 |
| Cetyl alcohol | 2 | 2 | 2 | 2 |
| Vaseline | 1 | 1 | 1 | 1 |
| Glyceryl monostearate | 1.5 | 1.5 | 1.5 | 1.5 |
| POE(60) hydrogenated castor oil | 1.3 | 1.3 | 1.3 | 1.3 |
| Glycerol | 10 | 10 | 10 | 10 |
| Propylene glycol | 3 | 3 | 3 | 3 |
| Methyl paraben | 0.2 | 0.2 | 0.2 | 0.2 |
| Purified water | To total amount 100 | | | |
| Vitamin A quantitative determination value | | | | |
| Immediately after preparation (%) | 100 | 100 | 100 | 100 |
| After one month at 40° C. (%) | 95 | 92 | 63 | 51 |

| Example 14-5: Cream | (% by weight) |
|---|---|
| A. Cetanol | 3 |
| Glycerylmonostearate | 2 |
| POE(25) cetyl ether | 1 |
| Stearic acid | 3 |
| Vaseline | 3 |
| Olive oil | 3 |
| Isopropyl palmitate | 1 |
| Squalane | 5 |
| Vitamin A | 0.1 |
| BHT | 0.05 |
| Perfume | q.s. |
| B. Propylene glycol | 3 |
| Potassium hydroxide | 0.2 |
| Synthetic saponite (Trade name: Smectone SA) | 0.1 |
| Citric acid | 0.001 |
| Purified water | To total amount 100 |

The oil phase portion (A) and the aqueous phase portion (B) are thermally melted at 70° C., then A is added to B, the resulting mixture is emulsified, and subsequently subjected to a cooling treatment to form a cream.

| Example 14-6: Beauty gel | (% by weight) |
|---|---|
| Synthetic hectlite (Trade name: Laponite XLG) | 10 |

-continued

| Example 14-6: Beauty gel | (% by weight) |
|---|---|
| Glycerol | 15 |
| Propylene glycol | 5 |
| Citric acid | 0.5 |
| Triethanolamine | 1.8 |
| 2-hydroxy-4-methoxybenzophenone-5-sodium sulfonate | 1 |
| POE(60) hydrogenated castor oil | 0.5 |
| Vitamin A | 0.1 |
| Octylmetroxycinnamate | 9 |
| Methyl paraben | 0.2 |
| Ethyl alcohol | 3 |
| Purified water | To total amount 100 |

| Example 14-7: Cosmetic lotion | (% by weight) |
|---|---|
| Glycerol | 2 |
| Ethanol | 7 |
| POE(50) Oleyl ether | 0.5 |
| Oleyl alcohol | 0.002 |
| Vitamin A | 0.0001 |
| Synthetic saponite (Trade name: Smectone SA) | 0.01 |
| Lactic acid | 0.01 |
| Sodium lactate | 0.09 |
| Methyl paraben | 0.1 |
| Purified water | To total amount 100 |

| Example 14-8: Cream | (% by weight) |
|---|---|
| Squalane | 15 |
| Glycerol tri 2-ethylhexanoate | 10 |
| Olive oil | 10 |
| Butyl paraben | 0.2 |
| Diglycerol diisostearate | 2 |
| Glycerylmonooleate | 2 |
| Natural saponite (Trade name: Veegum HV) | 3 |
| Dimethylstearylammoniumchloride | 1.0 |
| Vitamin A | 0.5 |
| BHT | 0.1 |
| Disodium edetate | 0.01 |
| Ascorbic acid | 0.01 |
| Sodium isoascorbate | 0.01 |
| 2-hydroxy-4-methoxybenzophenone | 0.3 |
| Glycerol | 10 |
| Phenoxy ethanol | 0.1 |
| Purified water | To total amount 100 |

| Example 14-9: Oil gel | (% by weight) |
|---|---|
| Vitamin A | 1 |
| Glycerol tri 2-ethylhexanoate | 40 |
| α-tocopherol | 9 |
| Squalane | 10 |
| Natural montmorillonite (Trade name: Kunipia G) | 10 |
| Natural saponite (Trade name: Veegum HV) | 10 |
| BHT | 1 |
| 2-ethylhexyl paradimethylbenzoate | 10 |
| POE(20) hydrogenated castor oil | 6 |
| Purified water | 4 |

| Example 14-10: Beauty powder | (% by weight) |
| --- | --- |
| Synthetic hectlite (Trade name: Laponite XLG) | 50 |
| D-mannitol | 48 |
| Isopropyl palmitate | 1.9 |
| Vitamin A | 0.1 |

| Example 14-11: Beauty essense | (% by weight) |
| --- | --- |
| Synthetic hectlite (Trade name: Laponite XLG) | 3 |
| Synthetic saponite (Trade name: Smectone SA) | 1 |
| Glycerol | 20 |
| Propylene glycol | 5 |
| Citric acid | 0.03 |
| Trisodium citrate | 0.07 |
| α-tocopherol | 1 |
| 2-hydroxy-4-methoxybenzophenone-5-Sodium sulfonate | 0.5 |
| 4-t-butyl-4'-methoxydibenzoylmethane | 0.1 |
| POE(60) hydrogenated castor oil | 0.5 |
| Vitamin A | 0.1 |
| Sodium hexametaphosphate | 0.02 |
| Methyl paraben | 0.2 |
| Ethyl alcohol | 3 |
| Purified water | To total amount 100 |

The external skin treatment compositions of Examples 14-5 to 14-11 were excellent in the stability of vitamin A in daily use.

In the external skin treatment composition of the present invention, by formulating at least one water-swellable clay mineral, the stability of vitamin A can be improved.

In accordance with the present invention, by formulating at least one water-swellable clay mineral and at least one antioxidant, chelating agent and ultraviolet absorber, the stability of vitamin A can be further noticeably improved.

We claim:

1. An external skin treatment composition comprising (I) vitamin A and (II) at least one stabilizer selected from the group consisting of:
   (1) (i) at least one oil-soluble antioxidant selected from the group consisting of butyl hydroxytoluene (BHT), butyl hydroxyanisole (BHA), α,β,γ,δ-tocopherol, nordihydrogualaretin, propyl gallate, fatty acid esters of vitamin C and sorbic acid, (ii) at least one ethylenediaminetetraacetate and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
   (2) (i) at least one oil-soluble antioxidant selected from the group consisting of BHT, BHA, α,β,γ,δ-tocopherol, nordihydrogualaretin, propyl gallate and fatty acid esters of vitamin C, (ii) at least one compound selected from the group consisting of ascorbic acid, ascorbic acid salts, isoascorbic acid, isoascorbic acid salts, sorbic acid and sorbic acid salts and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
   (3) inclusion compounds of (i) cyclodextrins including (ii) at least one compound selected from the group consisting of nordihydrogualaretin, BHT, BHA, α,β,γ,δ-tocopherols, propyl gallate, a fatty acid ester of vitamin C, sorbic acid, benzophenones-1 to 10 and 12, cinnamic acid compounds, salicylic acid compounds, benzoic acid compounds, and dibenzoylmethane compounds;
   (4) (i) 1,3-butanediol and/or (ii) at least one oil-soluble antioxidant selected from the group consisting of nordihydrogualaretin, BHT, BHA, α,β,γ,δ-tocopherols, propyl gallate, a fatty acid ester of vitamin C and sorbic acid; and
   (5) at least one water-soluble benzophenone compound, wherein the composition comprises 0.0001% by weight or more of vitamin A, and
      (A) 0.001% by weight or more of (1) (i) the oil-soluble antioxidant,
      (B) 0.001% by weight or more of (1)(ii) the ethylenediaminetetraacetate,
      (C) 0.001% by weight or more of (1) (iii) the benzophenone compound, on the basis of the total weight of the composition.

2. An external skin treatment composition comprising (I) vitamin A and (II) at least one stabilizer selected from the group consisting of:
   (1) (i) at least one oil-soluble antioxidant selected from the group consisting of butyl hydroxytoluene (BHT), butyl hydroxyanisole (BHA), α,β,γ,δ-tocopherol, nordihydrogualaretin, propyl gallate, fatty acid esters of vitamin C and sorbic acid, (ii) at least one ethylenediaminetetraacetate and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
   (2) (i) at least one oil-soluble antioxidant selected from the group consisting of BHT, BHA α,β,γ,δ-tocopherol, nordihydrogualaretin, propyl gallate and fatty acid esters of vitamin C, (ii) at least one compound selected from the group consisting of ascorbic acid, ascorbic acid salts, isoascorbic acid, isoascorbic acid salts, sorbic acid and sorbic acid salts and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
   (3) inclusion compounds of (i) cyclodextrins including (ii) at least one compound selected from the group consisting of nordihydrogualaretin, BHT, BHA, α,β,γ,δ-tocopherols, propyl gallate, a fatty acid ester of vitamin C, sorbic acid, benzophenones-1 to 10 and 12, cinnamic acid compounds, salicylic acid compounds, benzoic acid compounds, and dibenzoylmethane compounds;
   (4) (i) 1,3-butanediol and/or (ii) at least one oil-soluble antioxidant selected from the group consisting of nordihydrogualaretin, BHT, BHA, α,β,γ,δ-tocopherols, propyl gallate, a fatty acid ester of vitamin C and sorbic acid; and
   (5) at least one water-soluble benzophenone compound, wherein the composition comprises 0.0001% by weight or more of vitamin A, and (A) 0.001% by weight or more of (2) (i) the oil-soluble antioxidant,
(B) 0.001% by weight or more of (2) (ii) the compound, and
(C) 0.001% by weight or more of (2) (iii) the benzophenone compound, on the basis of the total weight of the composition.

3. An external skin treatment composition comprising (I) vitamin A and (II) at least one stabilizer selected from the group consisting of:
(1) (i) at least one oil-soluble antioxidant selected from the group consisting of butyl hydroxytoluene (BHT) butyl hydroxyanisole (BHA), α,β,γ,δ-tocopherol, nordihydrogualaretin, propyl gallate, fatty acid esters of vitamin C and sorbic acid, (ii) at least one ethylenediaminetetraacetate and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
(2) (i) at least one oil-soluble antioxidant selected from the group consisting of BHT, BHA, α,β,γ,δ-tocopherol, nordihydrogualaretin, propyl gallate and fatty acid esters of vitamin C, (ii) at least one compound selected from the group consisting of ascorbic acid, ascorbic acid salts, isoascorbic acid, isoascorbic acid salts, sorbic acid and sorbic acid salts and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
(3) inclusion compounds of (i) cyclodextrins including (ii) at least one compound selected from the group consisting of nordihydrogualaretin, BHT, BHA, α,β,γδ-tocopherols, propyl gallate, a fatty acid ester of vitamin C, sorbic acid, benzophenones-1 to 10 and 12, cinnamic acid compounds, salicylic acid compounds, benzoic acid compounds, and dibenzoylmethane compounds;
(4) (i) 1,3-butanediol and/or (ii) at least one oil-soluble antioxidant selected from the group consisting of nordihydrogualaretin, BHT, BHA, α,β,γ,δ-tocopherols, propyl gallate, a fatty acid ester of vitamin C and sorbic acid; and
(5) at least one water-soluble benzophenone compound, wherein the composition comprises 0.0001% by weight or more of vitamin A, 0.01% by weight or more of (3) (i) the cyclodextrin including 0.001% by weight or more of (3) (ii) the compound, on the basis of the total weight of the composition.

4. An external skin treatment composition comprising (I) vitamin A and (II) at least one stabilizer selected from the group consisting of:
(1) (i) at least one oil-soluble antioxidant selected from the group consisting of butyl hydroxytoluene (BHT), butyl hydroxyanisole (BHA), α,β,γ,δ-tocopherol, nordihydrogualaretin, propyl gallate, fatty acid esters of vitamin C and sorbic acid, (ii) at least one ethylenediaminetetraacetate and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
(2) (i) at least one oil-soluble antioxidant selected from the group consisting of BHT, BHA, α,β,γ,δ-tocopherol, nordihydrogualaretin, propyl gallate and fatty acid esters of vitamin C, (ii) at least one compound selected from the group consisting of ascorbic acid, ascorbic acid salts, isoascorbic acid, isoascorbic acid salts, sorbic acid and sorbic acid salts and, (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
(3) inclusion compounds of (i) cyclodextrins including (ii) at least one compound selected from the group consisting of nordihydrogualaretin, BHT, BHA, α,β,γ,δ-tocopherols, propyl gallate, a fatty acid ester of vitamin C, sorbic acid, benzophenones-1 to 10 and 12, cinnamic acid compounds, salicylic acid compounds, benzoic acid compounds, and dibenzoylmethane compounds:
(4) (i) 1,3-butanediol and/or (ii) at least one oil-soluble antioxidant selected from the group consisting of nordihydrogualaretin, BHT, BHA, α,β,γ,δ-tocopherols, propyl gallate, a fatty acid ester of vitamin C and sorbic acid; and
(5) at least one water-soluble benzophenone compound, wherein the composition comprises 0.0001% by weight or more of vitamin A, 0.01% by weight or more of (4) (i) the 1,3-butanediol and 0.001% by weight or more of (4) (ii) the oil-soluble antioxidant, on the basis of the total weight of the composition.

5. An external skin treatment composition comprising (I) vitamin A and (II) at least one stabilizer selected from the group consisting of:
(1) (i) at least one oil-soluble antioxidant selected from the group consisting of butyl hydroxytoluene (BHT), butyl hydroxyanisole (BHA), α,β,γ,δ-tocopherol, nordihydrogualaretin, propyl gallate, fatty acid esters of vitamin C and sorbic acid, (ii) at least one ethylenediaminetetraacetate and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
(2) (i) at least one oil-soluble antioxidant selected from the group consisting of BHT, BHA, α,β,γ,δ-tocopherol, nordihydrogualaretin, propyl gallate and fatty acid esters of vitamin C, (ii) at least one compound selected from the group consisting of ascorbic acid, ascorbic acid salts, isoascorbic acid, isoascorbic acid salts, sorbic acid and sorbic acid salts and (iii) at least one benzophenone compound selected from the group consisting of benzophenone-1, benzophenone-2, benzophenone-3, benzophenone-4, benzophenone-5, benzophenone-6, benzophenone-7, benzophenone-8, benzophenone-9, benzophenone-10 and benzophenone-12;
(3) inclusion compounds of (i) cyclodextrins including (ii) at least one compound selected from the group consisting of nordihydrogualaretin, BHT, BHA, α,β,γ,δ-tocopherols, propyl gallate, a fatty acid ester of vitamin C, sorbic acid, benzophenones-1 to 10 and 12, cinnamic acid compounds, salicylic acid compounds, benzoic acid compounds, and dibenzoylmethane compounds;

(4) (i) 1,3-butanediol and/or (ii) at least one oil-soluble antioxidant selected from the group consisting of nordihydrogualaretin, BHT, BHA, α,β,γ,δ-tocopherols, propyl gallate, a fatty acid ester of vitamin C and sorbic acid; and (5) at least one water-soluble benzophenone compound, wherein the composition comprises 0.0001% by weight or more of vitamin A and 0.001% by weight or more of (5) the water-soluble benzophenone compound, on the basis of the total weight of the composition.

6. An external skin treatment composition comprising, all on a basis of a total weight of the composition, (I) 0.0001 % by weight or more of vitamin A and (II) at least one stabilizer comprising 0.001 % by weight or more of at least one benzophenone compound selected from the group consisting of benzophenone-1, benzophenone-2, benzophenone-3, benzophenone4, benzophenone-5, benzophenone-6, benzophenone-7, benzophenone-8, benzophenone-9, benzophenone-10 and benzophenone-12.

7. The composition of claim 6, further comprising at least one of (i) or (ii):

(i) 0.001 % by weight or more of at least one oil-soluble antioxidant selected from the group consisting of butyl hydroxytoluene (BHT), butyl hydroxyanisole (BHA), α,β,γ,δ-tocopherol, nordihydrogualaretin, propyl gallate and fatty acid esters of vitamin C; and (ii) 0.001 % by weight or more of at least one ethylenediaminetetraacetate.

8. The composition of claim 6, further comprising at least one of (i) or (ii):

(i) 0.001% by weight or more of at least one oil-soluble antioxidant selected from the group consisting of butyl hydroxytoluene (BHT), butyl hydroxyanisole (BHA), α,β,γ,δ-tocopherol, nordihydrogualaretin, propyl gallate and fatty acid esters of vitamin C; and (ii) 0.001% by weight or more of at least one compound selected from the group consisting of ascorbic acid, ascorbic acid salts, isoascorbic acid, isoascorbic acid salts, sorbic acid and sorbic acid salts.

9. An external skin treatment composition comprising, all on a basis of a total weight of the composition, (I) 0.0001 % by weight or more of vitamin A and (II) at least one stabilizer comprising 0.01% by weight or more of inclusion compounds of (i) cyclodextrins including (ii) 0.001% by weight or more of at least one compound selected from the group consisting of benzophenones-1 to 10 and 12, cinnamic acid compounds, salicylic acid compounds, benzoic acid compounds, and dibenzoylmethane compounds.

10. The composition of claim 9, further comprising at least one of nordihydrogualaretin, BHT, BHA, α,β,γ,δ-tocopherols, propyl gallate, a fatty acid ester of vitamin C and sorbic acid.

11. An external skin treatment composition comprising, all on a basis of a total weight of the composition, (I) 0.0001 % by weight or more of vitamin A and (II) at least one stabilizer comprising 0.001 % by weight or more of at least one water soluble benzophenone compound.

* * * * *